(12) United States Patent
Buchanan et al.

(10) Patent No.: US 7,115,617 B2
(45) Date of Patent: Oct. 3, 2006

(54) AMINO-SUBSTITUTED PYRIMIDINYL DERIVATIVES AND METHODS OF USE

(75) Inventors: John L. Buchanan, Newton, MA (US); Stuart Chaffee, Philadelphia, PA (US); Jean-Christophe Harmange, Andover, MA (US); Perry M. Novak, Milford, MA (US); Xiaotian Zhu, Newton, MA (US)

(73) Assignee: Amgen Inc., Thousand Oaks, CA (US)

( * ) Notice: Subject to any disclaimer, the term of this patent is extended or adjusted under 35 U.S.C. 154(b) by 200 days.

(21) Appl. No.: 10/225,819

(22) Filed: Aug. 21, 2002

(65) Prior Publication Data

US 2003/0125346 A1 Jul. 3, 2003

Related U.S. Application Data

(60) Provisional application No. 60/314,285, filed on Aug. 22, 2001.

(51) Int. Cl.
C07D 413/12 (2006.01)
A61K 31/422 (2006.01)
C07D 239/48 (2006.01)

(52) U.S. Cl. ........................ 514/275; 544/324
(58) Field of Classification Search ................ 544/324; 514/275

See application file for complete search history.

(56) References Cited

U.S. PATENT DOCUMENTS

| 4,983,608 | A | 1/1991 | Effland et al. |
| 5,043,317 | A | 8/1991 | Chapman et al. |
| 5,935,966 | A | 8/1999 | Suto et al. |
| 5,958,935 | A | 9/1999 | Davis et al. |
| 6,080,858 | A | 6/2000 | Schumacher |
| 2002/0137755 | A1 | 9/2002 | Bilodeau et al. |

FOREIGN PATENT DOCUMENTS

| EP | 0 379 806 B1 | 4/1996 |
| EP | 0 945 443 A1 | 9/1999 |
| EP | 1 040 831 A2 | 10/2000 |
| WO | WO 94/26733 | 11/1994 |
| WO | WO 95/33750 | 12/1995 |
| WO | WO 97/19065 | 5/1997 |
| WO | WO 99/31073 | 6/1999 |
| WO | WO 99/41253 | 8/1999 |
| WO | WO 99/50250 | 10/1999 |
| WO | WO 00/27825 | 5/2000 |
| WO | WO 00/39101 | 7/2000 |
| WO | WO 00/53595 | 9/2000 |
| WO | WO 00/59892 | 10/2000 |
| WO | WO 00/78731 | 12/2000 |
| WO | WO 01/00213 | 1/2001 |
| WO | WO 01/19825 | 3/2001 |
| WO | WO 01/22938 | 4/2001 |
| WO | WO 01/29009 | 4/2001 |
| WO | WO 01/40218 | 6/2001 |
| WO | WO 01/47921 | 7/2001 |
| WO | WO 01/64655 | 9/2001 |
| WO | WO 01/72717 | 10/2001 |
| WO | WO 01/72745 | 10/2001 |
| WO | WO 01/85700 | 11/2001 |
| WO | WO 02/22601 | 3/2002 |
| WO | WO 02/45652 | 6/2002 |
| WO | WO 02/46170 | 6/2002 |
| WO | WO 02/46171 | 6/2002 |
| WO | WO 02/46184 | 6/2002 |
| WO | WO 02/47690 | 6/2002 |
| WO | WO 02/48147 | 6/2002 |
| WO | WO 02/48148 | 6/2002 |
| WO | WO 02/50065 | 6/2002 |
| WO | WO 02/50066 | 6/2002 |
| WO | WO 02/057259 | 7/2002 |
| WO | WO 02/059110 | 8/2002 |

OTHER PUBLICATIONS

Adams et al., Medline Abstract (Structure and function of the type 1 insulin-like growth factor receptor, Cellular And Molecular Life Sciences, vol. 57, Issue 7, pp. 1050-1093) Jul. 2000.
Simone, Oncology: Introduction, Cecil Textbook of Medicine, 20th Edition, vol. 1, pp. 1004-1010, 1996.
Traxler, Protein tyrosine kinase inhibitors in cancer treatment, Exp. Opin. Ther. Patents, 7(6):571-588, 1997.
Ghoneim et al., "Synthesis and Evaluation of Some 2-, 4-, and 2,4-Disubstituted-6-Methylpyrimidine Derivatives for Antimicrobial Activity" Egyptian J. Pharm. Sci., 28:117-126 (1987).

*Primary Examiner*—Deepak Rao
(74) *Attorney, Agent, or Firm*—Joseph W. Bulock

(57) ABSTRACT

The invention encompasses compounds, analogs, prodrugs and pharmaceutically acceptable derivatives thereof, pharmaceutical compositions, uses and methods for prophylaxis and treatment of cancer.

29 Claims, No Drawings

AMINO-SUBSTITUTED PYRIMIDINYL DERIVATIVES AND METHODS OF USE

This application claims the benefit of U.S. Provisional Application No. 60/314,285, filed Aug. 22, 2001, which is hereby incorporated by reference.

FIELD OF THE INVENTION

This invention is in the field of pharmaceutical agents and specifically relates to compounds, compositions, uses and methods for treating cancer and related disorders.

BACKGROUND OF THE INVENTION

Phosphoryl transferases are a large family of enzymes that transfer phosphorous-containing groups from one substrate to another. Kinases are a class of enzymes that function in the catalysis of phosphoryl transfer. The protein kinases constitute the largest subfamily of structurally related phosphoryl transferases and are responsible for the control of a wide variety of signal transduction processes within the cell. Almost all kinases contain a similar 250–300 amino acid catalytic domain. The protein kinases may be categorized into families by the substrates they phosphorylate (e.g., protein-tyrosine, protein-serine/threonine, etc.). Protein kinase sequence motifs have been identified that generally correspond to each of these kinase families. Lipid kinases (e.g. PI3K) constitute a separate group of kinases with structural similarity to protein kinases.

The "kinase domain" appears in a number of polypeptides which serve a variety of functions. Such polypeptides include, for example, transmembrane receptors, intracellular receptor associated polypeptides, cytoplasmic located polypeptides, nuclear located polypeptides and subcellular located polypeptides. The activity of protein kinases can be regulated by a variety of mechanisms. It must be noted, however, that an individual protein kinase may be regulated by more than one mechanism. These mechanisms include, for example, autophosphorylation, transphosphorylation by other kinases, protein-protein interactions, protein-lipid interactions, protein-polynucleotide interactions, ligand binding, and post-translational modification.

Protein and lipid kinases regulate many different cell processes including, but not limited to, proliferation, growth, differentiation, metabolism, cell cycle events, apoptosis, motility, transcription, translation and other signaling processes, by adding phosphate groups to targets such as proteins or lipids. Phosphorylation events catalyzed by kinases act as molecular on/off switches that can modulate or regulate the biological function of the target protein. Phosphorylation of target proteins occurs in response to a variety of extracellular signals (hormones, neurotransmitters, growth and differentiation factors, etc.), cell cycle events, environmental or nutritional stresses, etc. Protein and lipid kinases can function in signaling pathways to activate or inactivate, or modulate the activity of (either directly or indirectly) the targets. These targets may include, for example, metabolic enzymes, regulatory proteins, receptors, cytoskeletal proteins, ion channels or pumps, or transcription factors. Uncontrolled signaling due to defective control of protein phosphorylation has been implicated in a number of diseases and disease conditions, including, for example, inflammation, cancer, allergy/asthma, disease and conditions of the immune system, disease and conditions of the central nervous system (CNS), cardiovascular disease, dermatology, and angiogenesis.

Initial interest in protein kinases as pharmacological targets was stimulated by the findings that many viral oncogenes encode structurally modified cellular protein kinases with constitutive enzyme activity. These findings pointed to the potential involvement of oncogene related protein kinases in human proliferative disorders. Subsequently, deregulated protein kinase activity, resulting from a variety of more subtle mechanisms, has been implicated in the pathophysiology of a number of important human disorders including, for example, cancer, CNS conditions, and immunologically related diseases. The development of selective protein kinase inhibitors that can block the disease pathologies and/or symptoms resulting from aberrant protein kinase activity has therefore generated much interest.

Protein kinases represent a large family of proteins which play a central role in the regulation of a wide variety of cellular processes, maintaining control over cellular function. A partial list of such kinases includes abl, AKT, bcr-abl, Blk, Brk, Btk, c-kit, c-met, c-src, CDK1, CDK2, CDK3, CDK4, CDK5, CDK6, CDK7, CDK8, CDK9, CDK10, cRaf1, CSFir, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS—R, Jak, KDR, Lck, Lyn, MEK, p38, PDGFR, PIK, PKC, PYK2, ron, tie, tie2, TRK, Yes, and Zap70. Inhibition of such kinases has become an important therapeutic target.

A major feature of malignant cells is the loss of control over one or more cell cycle elements. These elements range from cell surface receptors to the regulators of transcription and translation, including the insulin-like growth factors, insulin growth factor-I (IGF-1) and insulin growth factor-2 (IGF-2). [M. J. Ellis, "The Insulin-Like Growth Factor Network and Breast Cancer", Breast Cancer, Molecular Genetics, Pathogenesis and Therapeutics, Humana Press 1999]. The insulin growth factor system consists of families of ligands, insulin growth factor binding proteins, and receptors. A major physiological role of the IGF-1 system is the promotion of normal growth and regeneration, and overexpressed IGF-1R can initiate mitogenesis and promote ligand-dependent neoplastic transformation. Furthermore, IGF-1R plays an important role in the establishment and maintenance of the malignant phenotype.

IGF-1R exists as a heterodimer, with several disulfide bridges. The tyrosine kinase catalytic site and the ATP binding site are located on the cytoplasmic portion of the beta subunit.

Unlike the epidermal growth factor (EGF) receptor, no mutant oncogenic forms of the IGF-1R have been identified. However, several oncogenes have been demonstrated to affect IGF-1 and IGF-1R expression.

The correlation between a reduction of IGF-1R expression and resistance to transformation has been seen. Exposure of cells to the mRNA antisense to IGF-1R RNA, prevents soft agar growth of several human tumor cell lines.

Apoptosis is a ubiquitous physiological process used to eliminate damaged or unwanted cells in multicellular organisms. Disregulation of apoptosis is believed to be involved in the pathogenesis of many human diseases. The failure of apoptotic cell death has been implicated in various cancers, as well as autoimmune disorders. Conversely, increased apoptosis is associated with a variety of diseases involving cell loss such as neurodegenerative disorders and AIDS. As such, regulators of apoptosis have become an important therapeutic target. It is now established that a major mode of tumor survival is escape from apoptosis. IGF-1R abrogates progression into apoptosis, both in vivo and in vitro. It has also been shown that a decrease in the level of IGF-1R below wild-type levels causes apoptosis of tumor cells in vivo. The ability of IGF-1R disruption to cause apoptosis appears to be diminished in normal, non-tumorigenic cells.

WO01/00213, published 4 Jan. 2001, describes substituted pyrimidines as SRC kinase inhibitors. WO01/40218, published 7 Jun. 2001, describes arylamine derivatives for use as anti-telomerase agents. WO00/39101, published 6 Jul. 2000, describes substituted pyrimidines as anti-cancer agents. WO01/29009, published 26 Apr. 2001, describes substituted pyrimidines as kinase inhibitors. WO00/78731, published 28 Dec. 2000, describes cyano substituted pyrimidines as kinase inhibitors. WO00/53595, published 14 Sep. 2000, describes substituted pyrimidines as kinase inhibitors. WO00/39101, published 6 Jul. 2000, describes amino substituted pyrimidines as kinase inhibitors. WO00/59892, published 12 Oct. 2000, describes amino substituted pyrimidines as kinase inhibitors. WO97/19065, published 29 May 1997, describes 2-anilino-pyrimidines as kinase inhibitors. EP379806, published 10 Apr. 1996, describes substituted pyrimidines for the treatment of neurological disorders. EP1040831, published 4 Oct. 2000, describes substituted pyrimidines as CRF antagonists. Amino substituted pyrimidines were cited in Chem. Abstr. 112:191083. Amino substituted pyrimidines were cited in Chem. Abstr. 72:1114009. WO95/33750, published 14 Dec. 1995, describes substituted pyrimidines as CRF antagonists. WO94/26733, published 24 Nov. 1994, describes pyrimidine derivatives as ligands for dopamine receptors. U.S. Pat. No. 5,958,935 describes substituted pyrimidines as kinase inhibitors. U.S. Pat. No. 4,983,608, describes pyrrolyl-amino substituted pyrimidines as analgesic agents. U.S. Pat. No. 5,043,317, describes amino substituted pyrimidines as dyes. U.S. Pat. No. 5,935,966 describes carboxylate substituted pyrimidines as anti-inflammatories. U.S. Pat. No. 6,080,858 describes a process for preparing substituted pyrimidines. WO99/50250, published 7 Oct. 1999, describes amino substituted pyrimidines for the treatment of HIV infection. EP945443, published 29 Sep. 1999, describes amino substituted pyrimidines for the treatment of HIV infection. WO99/31073, published 24 Jun. 1999, describes amide substituted pyrimidines. WO00/27825, published 18 May 2000, describes amino substituted pyrimidines for the treatment of HIV infection. WO01/22938, published 5 Apr. 2001, describes amino substituted pyrimidines for the treatment of HIV infection. WO99/41253, published 19 Aug. 1999, describes amino substituted pyrimidines for the treatment of viral infection. WO01/19825, published 22 Mar. 2001, describes amino substituted pyrimidines as synthetic intermediates. WO01/47921, published 5 Jul. 2001, describes amino substituted pyrimidines as kinase inhibitors. WO01/72745, published 4 Oct. 2001, describes 4-heteroaryl-substituted pyrimidines as inhibitors of CDK's. WO01/72717, published 4 Oct. 2001, describes 4-amino-5-cyanopyrimidines as inhibitors of CDK's. WO01/85700, published 15 Nov. 2001, describes pyrimidines as HIV replication inhibitors. WO02/22601, published 21 Mar. 2002, describes 4-(pyrazol-5-ylamino)pyrimidines as kinase inhibitors. WO02/46184, published describes 4-(4-pyrazolyl)-pyrimidines as kinase inhibitors. WO02/46170, published 13 Jun. 2002, describes 2-anilino-pyrimidines as inhibitors of JNK. WO02/46171, published 13 Jun. 2002, describes 2-anilino-pyrimidines as inhibitors of IKK. WO02/47690, published 20 Jun. 2002, describes 4-arylamino-pyrimidines as kinase inhibitors. WO02/48147, published 20 Jun. 2002, describes pyrimidines as kinase inhibitors. WO02/48148, published 20 Jun. 2002, describes pyrimidines as kinase inhibitors. WO02/50065, published 27 Jun. 2002, describes 2-(5-pyrazolylamino)-pyrimidines as kinase inhibitors. Ghoneim et al., Egypt J. Pharm. Sci., 28, 117–26 (1987)) describe N,N'-bis(3,5-dimethyl-4-isoxazolyl)-6-methyl-2,4-pyrimidinediamine. WO02/50066, published 27 Jun. 2002, describes 2-(5-pyrazolylamino)-pyrimidines as kinase inhibitors. WO02/57259, published 25 Jul. 2002, describes 4-(5-pyrazolylamino)-pyrimidines as kinase inhibitors. WO02/59110, published 1 Aug. 2002, describes amino substituted pyrimidines as inhibitors of VEGFR2.

However, compounds of the current invention have not been described as inhibitors for the treatment of cancer.

DESCRIPTION OF THE INVENTION

A class of compounds useful in treating cancer and is defined by Formula I

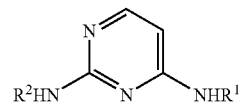

I wherein $R^1$ is heteroaryl containing at least one oxygen or sulfur heteroatom, wherein $R^1$ is optionally substituted with 1–4 substituents independently selected from $R^3$;
  preferably 5- or 6-membered heteroaryl containing at least one oxygen or sulfur heteroatom, wherein $R^1$ is optionally substituted with 1–4 substituents independently selected from $R^3$;
    more preferably 5- or 6-membered heteroaryl selected from isoxazolyl, isothiazolyl, oxazolyl, thiazolyl, 1,3,4-oxadiazolyl, 1,2,4-oxadiazolyl, 1,3,4-thiadiazolyl and 1,2,4-thiadiazolyl, wherein $R^1$ is optionally substituted with 1–2 substituents independently selected from $R^3$;
    even more preferably isoxazolyl, isothiazolyl, oxazolyl, thiazolyl, and, wherein $R^1$ is optionally substituted with 1–2 substituents independently selected from $R^3$; and
    particularly isoxazolyl;
wherein $R^2$ is selected from
  H,
  $C_{1-10}$-alkyl,
  $C_{2-10}$-alkenyl,
  $C_{2-10}$-alkynyl,
  $C(O)R^5$,
  $COOR^5$,
  $C(O)NR^5R^5$,
  $S(O)_nR^5$,
  $C_{3-10}$-cycloalkyl,
  $C_{4-10}$-cycloalkenyl,
  aryl optionally substituted with 1–5 substituents independently selected from $R^3$,
  $R^4$,
  $C_{1-10}$-alkyl substituted with 1–3 substituents independently selected from aryl, $R^7$ and $R^4$,
  $C_{3-10}$-cycloalkyl substituted with 1–3 substituents independently selected from aryl, $R^7$ and $R^4$, and
  $C_{2-10}$-alkenyl substituted with 1–3 substituents independently selected from aryl, $R^7$ and $R^4$;
  preferably $C_{1-6}$-alkyl,
    $C_{2-6}$-alkenyl,
    $C_{2-6}$-alkynyl,
    $C_{3-6}$-cycloalkyl, $C_{4-6}$-cycloalkenyl,
$R^4$,
phenyl optionally substituted with 1–4 substituents independently selected from $R^3$,
$C_{1-6}$-alkyl substituted with 1–3 substituents independently selected from aryl, $R^7$ and $R^4$,
$C_{3-6}$-cycloalkyl substituted with 1–3 substituents independently selected from aryl, $R^7$ and $R^4$, and
$C_{2-6}$-alkenyl substituted with 1–3 substituents independently selected from aryl and $R^4$,
more preferably $R^4$ and phenyl optionally substituted with 1–4 substituents independently selected from $R^3$,
even more preferably 3,4,5-trimethoxyphenyl, 3,4-dimethoxyphenyl, 2,5-dimethoxyphenyl, 3,4-dimethoxy-6-methylphenyl, quinolinyl, benzimidazolyl, indazolyl, 3-aminosulfonylphenyl and 4-aminosulfonylphenyl;
wherein $R^3$ is independently selected from
H,
$C_{1-10}$-alkyl,
$C_{2-10}$-alkenyl,
$C_{2-10}$-alkynyl,
$C_{3-10}$-cycloalkyl,
$C_{4-10}$-cycloalkenyl,
aryl,
$R^4$,
halo,
$SR^5$,
$OR^5$,
$OC(O)R^5$,
$NR^5R^5$,
$NR^5R^6$,
$COOR^5$,
$NO_2$,
CN,
$C(O)R^5$,
$C(O)C(O)R^5$,
$C(O)NR^5R^5$,
$S(O)_nR^5$,
$S(O)_nNR^5R^5$,
$NR^5C(O)NR^5R^5$,
$NR^5C(O)C(O)R^5$,
$NR^5C(O)R^5$,
$NR^5(COOR^5)$,
$NR^5C(O)R^4$,
$NR^5S(O)_nNR^5R^5$,
$NR^5S(O)_nR^5$,
$NR^5S(O)_nR^4$,
$NR^5C(O)C(O)NR^5R^5$,
$NR^5C(O)C(O)NR^5R^6$,
$C_{1-10}$-alkyl substituted with 1–3 substituents independently selected from aryl, $R^7$ and $R^4$; and
$C_{2-10}$-alkenyl substituted with 1–3 substituents independently selected from aryl, $R^7$ and $R^4$;
preferably selected from
$C_{1-6}$-alkyl,
$C_{2-6}$-alkenyl,
$C_{2-6}$-alkynyl,
$C_{3-6}$-cycloalkyl,
$C_{4-6}$-cycloalkenyl,
phenyl,
$R^4$,
halo,
$SR^5$,
$OR^5$,
$OC(O)R^5$,
$NR^5R^5$,
$NR^5R^6$,
$COOR^5$,
$NO_2$,
CN,
$C(O)R^5$,
$C(O)NR^5R^5$,
$S(O)_nR^5$,
$S(O)_nNR^5R^5$,
$NR^5C(O)NR^5R^5$,
$NR^5C(O)R^5$,
$NR^5(COOR^5)$,
$NR^5C(O)R^4$,
$NR^5S(O)_nNR^5R^5$,
$NR^5S(O)_nR^5$,
$NR^5S(O)_nR^4$,
$C_{1-6}$-alkyl substituted with 1–3 substituents independently selected from aryl, $R^7$ and $R^4$; and
$C_{2-6}$-alkenyl substituted with 1–3 substituents independently selected from aryl, $R^7$ and $R^4$;
more preferably $C_{1-4}$-alkyl, $C_{2-4}$-alkenyl, $C_{2-4}$-alkynyl, phenyl, $R^4$, chloro, fluoro, bromo, $CF_3$, $C_{1-4}$-alkoxy, phenoxy, heterocyclyloxy, benzyloxy, $C_{1-4}$-alkyl-C(O)O—, amino, alkylamino, phenylamino, carboxy, $C_{1-4}$-alkoxycarbonyl, $NO_2$, CN, $C_{1-4}$-alkylcarbonyl, aminocarbonyl, $C_{1-4}$-alkylaminocarbonyl, $C_{1-4}$-alkylsulfonyl, $C_{1-4}$-alkylaminosulfonyl, benzyl, $C_{1-4}$-alkoxyalkyl, $C_{1-4}$-aminoalkyl, $C_{1-4}$-alkylaminoalkyl, and 5–6-membered heterocyclyl-$C_{1-4}$-alkyl; and
even more preferably methyl, ethyl, propyl, tert-butyl, isopropyl, phenyl, chloro, fluoro, bromo, $CF_3$, methoxy, phenoxy, benzyloxy, acetyl, amino, methylamino, phenylamino, carboxy, ethoxycarbonyl, $NO_2$, CN, methylcarbonyl, aminocarbonyl, methylaminocarbonyl, methylsulfonyl, methylaminosulfonyl, benzyl, methoxymethyl, aminomethyl, N,N-dimethylaminoethyl and furylmethyl;
wherein $R^4$ is independently a 5–8 membered monocyclic, 8–12 membered bicyclic, or 11–14 membered tricyclic saturated, partially saturated or unsaturated ring system comprising 1–3 heteroatoms if monocyclic, 1–6 heteroatoms if bicyclic, or 1–9 heteroatoms if tricyclic, said heteroatoms independently selected from O, N, or S, which may be saturated or unsaturated, and wherein 0, 1, 2 or 3 atoms of each ring may be substituted by a substituent independently selected from $C_{1-10}$-alkyl, $C_{2-10}$-alkenyl, $C_{2-10}$-alkynyl, $C_{3-10}$-cycloalkyl, $C_{4-10}$-cycloalkenyl, halo, haloalkyl, sulfo, oxo, $SR^5$, $OR^5$, $NR^5R^5$, $NR^5R^6$, $NR^6R^6$, $COOR^5$, nitro, cyano, $S(O)_nR^5$, $S(O)_nNR^5R^5$, $C(O)R^5$ and $C(O)NR^5R^5$;
preferably a 5–7 membered monocyclic, or 8–11 membered bicyclic saturated, partially saturated or unsaturated ring system comprising 1–3 heteroatoms if monocyclic, or 1–6 heteroatoms if bicyclic, said heteroatoms independently selected from O, N, or S, which may be saturated or unsaturated, and wherein 0, 1, 2 or 3 atoms of each ring may be substituted by a substituent independently selected from $C_{1-6}$-alkyl, $C_{2-6}$-alkenyl, $C_{2-6}$-alkynyl, halo, $C_{1-6}$-haloalkyl, oxo, $SR^5$, $OR^5$, $NR^5R^5$, $COOR^5$, nitro, cyano, $S(O)_nR^5$, $S(O)_nNR^5R^5$, $C(O)R^5$ and $C(O)NR^5R^5$;
more preferably 5–6 membered monocyclic, or 8–10 membered bicyclic saturated, partially saturated or unsaturated ring system comprising 1–3 heteroatoms if monocyclic, 1–6 heteroatoms if bicyclic, said heteroatoms independently selected from O, N, or S, which may be saturated or unsaturated, and wherein 0, 1, 2 or 3 atoms of each ring may be substituted by a substituent independently selected from $C_{1-4}$-alkyl, halo, $C_{1-6}$-haloalkyl, oxo, $OR^5$, $NR^5R^5$, $COOR^5$, nitro, cyano, $S(O)_nR^5$, $S(O)_nNR^5R^5$, $C(O)R^5$ and $C(O)NR^5R^5$; and even more preferably quinolyl, isoquinolyl, indazolyl, imidazolyl, pyrazolyl, pyrrolyl, indolyl, isoindolyl, purinyl, and naphthyridinyl, wherein $R^4$ is optionally substituted by a substituent independently selected from methyl, isopropyl, tert-butyl, fluoro, chloro, —$CF_3$, oxo, methoxy, phenoxy, amino, methylamino, phenylamino, carboxy, ethoxycarbonyl, nitro, cyano, methylcarbonyl, aminocarbonyl, methylaminocarbonyl, methylsulfonyl and methylaminosulfonyl;

wherein $R^5$ is independently selected from H, $C_{1-10}$-alkyl, $C_{2-10}$-alkenyl, $C_{2-10}$-alkynyl, $C_{3-10}$-cycloalkyl, $C_{4-10}$-cycloalkenyl, $R^4$, aryl optionally substituted with 1–3 substituents independently selected from $R^3$, $C_1$–$C_{10}$ alkyl substituted with 1–3 substituents independently selected from aryl, $R^7$ and $R^4$;

$C_3$–$C_{10}$ cycloalkyl substituted with 1–3 substituents independently selected from aryl, $R^7$ and $R^4$; and $C_2$–$C_{10}$ alkenyl substituted with 1–3 substituents independently selected from aryl, $R^7$ and $R^4$;

preferably selected from H, $C_{1-6}$-alkyl, and phenyl optionally substituted with 1–3 substituents independently selected from $R^3$;

more preferably H, $C_{1-6}$-alkyl, and phenyl optionally substituted with 1–3 substituents independently selected from $C_{1-4}$-alkyl, chloro, fluoro, bromo, —$CF_3$, hydroxy, $C_{1-4}$-alkoxy, amino, $C_{1-4}$-alkylamino, carboxy, $C_{1-4}$-alkoxycarbonyl, —$NO_2$, —CN, $C_{1-4}$-alkylcarbonyl, $C_{1-4}$-alkylaminocarbonyl, aminocarbonyl, aminosulfonyl and acetyl;

wherein $R^6$ is selected from —$C(O)R^5$, —$COOR^5$, —$C(O)NR^5R^5$ and —$S(O)_nR^5$;

wherein $R^7$ is independently halo, —$CF_3$, —$SR^5$, —$OR^5$, —$OC(O)R^5$, —$NR^5R^5$, —$NR^5R^6$, —$NR^6R^6$, —$COOR^5$, —$NO_2$, —CN, —$C(O)R^5$, —$OC(O)NR^5R^5$, —$C(O)NR^5R^5$, —$N(R^5)C(O)R^5$, —$N(R^5)(COOR^5)$ and —$S(O)_nNR^5R^5$; and preferably halo, —$OR^5$, —$NR^5R^5$, —$COOR^5$ and —CN;

wherein n is 1 or 2;

and pharmaceutically acceptable salts thereof.

The invention also relates to compounds of Formula II

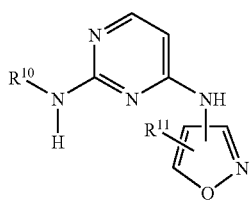

II wherein $R^{10}$ is selected from phenyl, and 5–10 membered heterocyclyl; wherein $R^{10}$ is optionally substituted with 1–2 substituents selected from $R^{11}$;

wherein $R^{11}$ is selected from $C_1$–$C_4$ alkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, $CF_3$, —$OR^{12}$, —$OC(O)R^{12}$, —$NR^{12}R^{12}$, —$COOR^{12}$, —$C(O)R^{12}$, —$C(O)NR^{12}R^{12}$, —$SO_2R^{12}$, —$SO_2NR^{12}R^{12}$, —$NR^{12}C(O)NR^{12}R^{12}$, —$NR^{12}C(O)R^{12}$, —$NR^{12}(COOR^{12})$, —$NR^{12}SO_2NR^{12}R^{12}$, —$NR^{12}SO_2R^{12}$, —$OC(O)NR^{12}R^{12}$, $C_1$–$C_3$ alkyl substituted with 1–3 substituents independently selected from optionally substituted phenyl and optionally substituted 5–6 membered heterocyclyl; and $C_2$–$C_3$ alkenyl substituted with 1–3 substituents independently selected from optionally substituted phenyl and optionally substituted 5–6 membered heterocyclyl;

wherein $R^{12}$ is selected from H, $C_{1-6}$-alkyl, and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, $NO_2$, CN, $C_{1-4}$-alkylcarbonyl, $C_{1-4}$-alkylaminocarbonyl, aminocarbonyl, aminosulfonyl and acetyl;

and pharmaceutically acceptable salts thereof.

The invention also relates to compounds of Formula III

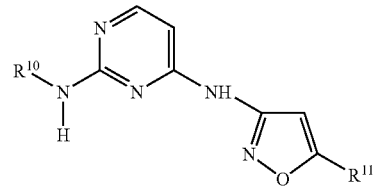

III wherein $R^{10}$ is selected from phenyl, and 5–10 membered heterocyclyl; wherein $R^{10}$ is optionally substituted with 1–2 substituents selected from $R^{11}$;

wherein $R^{11}$ is selected from $C_1$–$C_4$ alkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, $CF_3$, —$OR^{12}$, —$OC(O)R^{12}$, —$NR^{12}R^{12}$, $COOR^{12}$, —$C(O)R^{12}$, —$C(O)NR^{12}R^{12}$, $SO_2R^{12}$, —$SO_2NR^{12}R^{12}$, —$NR^{12}C(O)NR^{12}R^{12}$, —$NR^{12}C(O)R^2$, —$NR^{12}(COOR^{12})$, —$NR^{12}SO_2NR^{12}R^{12}$, —$NR^{12}SO_2R^{12}$, —$OC(O)NR^{12}R^{12}$, $C_1$–$C_3$ alkyl substituted with 1–3 substituents independently selected from optionally substituted phenyl and optionally substituted 5–6 membered heterocyclyl; and $C_2$–$C_3$ alkenyl substituted with 1–3 substituents independently selected from optionally substituted phenyl and optionally substituted 5–6 membered heterocyclyl;

wherein $R^{12}$ is selected from H, $C_{1-6}$-alkyl, and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, $NO_2$, CN, $C_{1-4}$-alkylcarbonyl, $C_{1-4}$-alkylaminocarbonyl, aminocarbonyl, aminosulfonyl and acetyl;

and pharmaceutically acceptable salts thereof.

The invention also relates to compounds of Formula I'

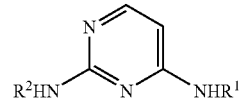

I' wherein $R^1$ is heteroaryl containing at least one oxygen or sulfur heteroatom, wherein $R^1$ is optionally substituted with 1–4 substituents independently selected from $R^3$;

preferably 5- or 6-membered heteroaryl containing at least one oxygen or sulfur heteroatom, wherein $R^1$ is optionally substituted with 1–3 substituents independently selected from $R^3$;

more preferably isoxazolyl, isothiazolyl, oxazolyl, pyranyl, thiazolyl, thiadiazolyl, oxadiazolyl, furazanyl, furyl, and thienyl;

even more preferably isoxazolyl, isothiazolyl, oxazolyl, thiazolyl, furyl, furazanyl and thienyl, wherein $R^1$ is optionally substituted with 1–2 substituents independently selected from $R^3$; particularly isoxazolyl; and more particularly 3-isoxazolyl or 5-isoxazolyl;

wherein $R^2$ is selected from $R^4$, and aryl optionally substituted with 1–5 substituents independently selected from $R^3$, preferably $R^4$ and aryl optionally substituted with 1–3 substituents independently selected from $R^3$;

more preferably naphthyl, 2,3-dihydro-indolyl, 1,3-benzodioxolyl, indolyl, 1,3-dioxo-isoindolyl, indazolyl, pyridyl, quinolyl, isoquinolyl, benzothiazolyl, 1,2,3-benzotriazolyl, benzimidazolyl, and phenyl; wherein $R^2$ is optionally substituted with 1–3 substituents independently selected from $R^3$;

even more preferably 2-naphthyl, 2,3-dihydro-indol-6-yl, 1,3-benzodioxol-5-yl, 5-indolyl, 4-indolyl, 1,3-dioxo-isoindol-5-yl, 5-indazolyl, 6-indazolyl, 3-pyridyl, 3-quinolyl, 6-quinolyl, isoquinolyl, benzothiazol-6-yl, benzothiazol-5-yl, 1,2,3-benzotriazol-5-yl, 6-benzimidazolyl, 5-pyridyl, and phenyl;

wherein $R^2$ is optionally substituted with 1–3 substituents independently selected from hydroxy, methoxy, ethoxy, cyano, nitro, chloro, fluoro, bromo, dimethylamino, dimethylaminoethyl, 3-dimethylamino-propoxy, methoxycarbonyl, methylcarbonyl, methylcarbonylamino, $CH_3C(O)N(CH_3)$—, methyl, ethyl, isopropyl, pyrrolidin-1-ylcarbonylethenyl, pyrrolidin-1-ylcarbonylethyl, pyrrolidin-1-ylpropyl, ethynyl, acetyl, ethoxycarbonylbutyl, carboxybutyl, 2-(1-methyl-piperidin-4-yl)-ethoxy, 2-(4-methyl-piperazin-1-yl)ethoxy, 3-(4-methyl-piperazin-1-yl)-propoxy, 3-(piperidin-1-yl)propoxy, 2-piperidin-1-yl-ethoxy, 2-morpholin-4-yl-ethoxy, pentafluoroethyl, trifluoromethyl, trifluoromethoxy, difluoromethoxy, aminocarbonyl, aminosulfonyl, N,N'-di-propylaminosulfonyl, hydroxypropylaminosulfonyl, (2-thiazolyl)aminosulfonyl, butylaminosulfonyl, methylcarbonylaminosulfonyl, methylsulfonyl, 1-methyl-piperidin-4-ylmethoxy, 1-tert-butoxycarbonyl-piperazin-4-yl, 4-morpholinyl, 4-methylpiperzin-1-yl, 4-piperazinyl, 4-isopropyl-piperazin-1-yl, and oxazol-5-yl; and particularly 3,4,5-trimethoxyphenyl, 3,4-dimethoxyphenyl, 2,5-dimethoxyphenyl, 3,4-dimethoxy-6-methylphenyl, 3-methylcarbonylaminophenyl, 4-[$CH_3C(O)NH$—$SO_2$]-phenyl, 3-isopropylphenyl, 4-[$CH_3C(O)N(CH_3)$]phenyl, 3-methoxy-4-morpholinylphenyl, 3-quinolinyl, 6-quinolinyl, benzimidazolyl, 5-indazolyl, 6-indazolyl, 3-chlorophenyl, 3-aminosulfonylphenyl and 4-aminosulfonylphenyl;

wherein $R^3$ is independently selected from
H,
$C_{1-10}$-alkyl,
$C_{2-10}$-alkenyl,
$C_{2-10}$-alkynyl,
$C_{1-10}$-haloalkyl,
$C_{3-10}$-cycloalkyl,
$C_{4-10}$-cycloalkenyl,
aryl,
$R^4$,
halo,
$SR^5$,
$OR^5$,
$OC(O)R^5$,
$NR^5R^5$,
$NR^5R^6$,
$COOR^5$,
nitro,
cyano,
$C(O)R^5$,
$C(O)C(O)R^5$,
$C(O)NR^5R^5$,
$S(O)_nR^5$,
$S(O)_nNR^5R^5$,
$S(O)_nNR^5R^6$,
$NR^5C(O)NR^5R^5$,
$NR^5C(O)C(O)R^5$,
$NR^5C(O)R^5$,
$NR^5COOR^5$,
$NR^5C(O)R^4$,
$NR^5S(O)_nNR^5R^5$,
$NR^5S(O)_nR^5$,
$NR^5S(O)_nR^4$,
$NR^5C(O)C(O)NR^5R^5$,
$NR^5C(O)C(O)NR^5R^6$,
$C_{1-10}$-alkyl substituted with 1–3 substituents independently selected from aryl, $R^7$ and $R^4$; and
$C_{2-10}$-alkenyl substituted with 1–3 substituents independently selected from aryl, $R^7$ and $R^4$;

preferably H, $C_{1-4}$-alkyl, $C_{2-4}$-alkenyl, $C_{2-4}$-alkynyl, phenyl, $C_{6-10}$-cycloalkyl, $R^4$, chloro, fluoro, bromo, trifluoromethyl, hydroxy, $C_{1-4}$-alkoxy, $C_{1-4}$-haloalkoxy, phenoxy, heterocyclyloxy, benzyloxy, $C_{1-4}$-alkylcarbonyloxy, amino, alkylamino, phenylamino, carboxy, $C_{1-4}$-alkoxycarbonyl, nitro, cyano, $C_{1-4}$-alkylcarbonyl, aminocarbonyl, $C_{1-4}$-alkylaminocarbonyl, $C_{1-4}$-alkylsulfonyl, $C_{1-4}$-alkylaminosulfonyl, benzyl, $C_{1-4}$-alkoxyalkyl, $C_{1-4}$-aminoalkyl, $C_{1-4}$-alkylaminoalkyl, and 5–6-membered heterocyclyl-$C_{1-4}$-alkyl;

more preferably H, halo, $C_{1-3}$-alkyl, $C_{2-3}$-alkenyl, $C_{2-3}$-alkynyl, phenyl, $C_{6-10}$-cycloalkyl, hydroxy, $C_{1-3}$-haloalkoxy, $C_{1-3}$-alkoxy, —C(O)—$C_{1-3}$-alkyl, and $C_{1-3}$-haloalkyl; and even more preferably H, hydroxy, iodo, methyl, acetyl, trifluoromethyl, methoxy, cyclohexyl, adamantyl, phenyl and trifluoromethoxy;

wherein $R^4$ is independently a 5–8 membered monocyclic, 8–12 membered bicyclic, or 11–14 membered tricyclic saturated, partially saturated or unsaturated ring system comprising 1–3 heteroatoms if monocyclic, 1–6 heteroatoms if bicyclic, or 1–9 heteroatoms if tricyclic, said heteroatoms independently selected from O, N, or S, which may be saturated or unsaturated, and wherein 0, 1, 2 or 3 atoms of each ring may be substituted by a substituent independently selected from $C_{1-10}$-alkyl, $C_{2-10}$-alkenyl, $C_{2-10}$-alkynyl, $C_{3-10}$-cycloalkyl, $C_{4-10}$-cycloalkenyl, halo, haloalkyl, sulfo, oxo, $SR^5$, $OR^5$, $NR^5R^5$, $NR^5R^6$, $NR^6R^6$, $COOR^5$, nitro, cyano, $S(O)_nR^5$, $S(O)_n$ $NR^5R^5$, $C(O)R^5$, $C(O)NR^5R^5$ and 6-membered heteroaryl optionally substituted with 1–3 substituents independently selected from $R^3$;
preferably 2,3-dihydro-indolyl, 1,3-benzodioxolyl, indolyl, 1,3-dioxo-isoindolyl, indazolyl, pyridyl, quinolyl, isoquinolyl, benzothiazolyl, 1,2,3-benzotriazolyl, benzimidazolyl, and pyridyl; wherein $R^4$ is optionally substituted with hydroxy, $C_{1-3}$-alkoxy, cyano, nitro, halo, $C_{1-3}$-alkyl, di-$C_{1-3}$-alkylamino, di-$C_{1-3}$-alkylamino-$C_{1-3}$-alkyl, di-$C_{1-3}$-alkylamino-$C_{1-3}$-alkoxy, $C_{1-3}$-alkylcarbonyl, $C_{1-3}$-alkoxycarbonyl, $C_{1-3}$-alkylcarbonylamino, pyrrolidinylcarbonyl-$C_{2-3}$-alkenyl, pyrrolidinylcarbonyl-$C_{1-3}$-alkyl, pyrrolidinyl-$C_{1-3}$-alkyl, $C_{2-3}$-alkynyl, acetyl, $C_{1-3}$-alkylcarbonyl-$C_{1-3}$-alkyl, carboxy-$C_{1-3}$-alkyl, (piperidinyl)-$C_{1-3}$-alkoxy, (piperazinyl)-$C_{1-3}$-alkoxy, 2-morpholinyl-$C_{1-3}$-alkoxy, $C_{1-3}$-haloalkyl, $C_{1-3}$-haloalkoxy, aminocarbonyl, aminosulfonyl, $C_{1-3}$-alkylaminosulfonyl, hydroxy-$C_{1-3}$-alkylaminosulfonyl, (thiazolyl)aminosulfonyl, $C_{1-4}$-alkylaminosulfonyl, $C_{1-3}$-alkylcarbonylaminosulfonyl, $C_{1-3}$-alkylsulfonyl, $C_{1-3}$-alkoxycarbonyl-piperazinyl, morpholinyl, $C_{1-3}$-alkylpiperzinyl, piperazinyl, $C_{1-3}$-alkyl-piperazinyl, and oxazolyl;
more preferably 2,3-dihydro-indol-6-yl, 1,3-benzodioxol-5-yl, 5-indolyl, 4-indolyl, 1,3-dioxo-isoindol-5-yl, 5-indazolyl, 6-indazolyl, 3-pyridyl, 3-quinolyl, 6-quinolyl, isoquinolyl, benzothiazol-6-yl, benzothiazol-5-yl, 1,2,3-benzotriazol-5-yl, 6-benzimidazolyl, and 5-pyridyl;
wherein $R^5$ is independently selected from H, $C_{1-10}$-alkyl, $C_{2-10}$-alkenyl, $C_{2-10}$-alkynyl, $C_{3-10}$-cycloalkyl, $C_{4-10}$-cycloalkenyl, $R^4$, aryl optionally substituted with 1–3 substituents independently selected from $R^3$,
$C_1$–$C_{10}$ alkyl substituted with 1–3 substituents independently selected from aryl, $R^7$ and $R^4$;
$C_3$–$C_{10}$ cycloalkyl substituted with 1–3 substituents independently selected from aryl, $R^7$ and $R^4$; and
$C_2$–$C_{10}$ alkenyl substituted with 1–3 substituents independently selected from aryl, $R^7$ and $R^4$;
wherein R is selected from —$C(O)R^5$, —$COOR^5$, —$C(O)NR^5R^5$ and —$S(O)_nR^5$;
wherein $R^7$ is independently halo, —$CF_3$, —$SR^5$, —$OR^5$, —$OC(O)R^5$, —$NR^5R^5$, —$NR^5R^6$, —$NR^6R^6$, —$COOR^5$, —$NO_2$, —CN, —$C(O)R^5$, —$OC(O)NR^5R^5$, —$C(O)NR^5R^5$, —$N(R^5)C(O)R^5$, —$N(R^5)(COOR^5)$ and —$S(O)_nNR^5R^5$; and
wherein n is 1 or 2; preferably 2;
and pharmaceutically acceptable derivative thereof.
The invention also relates to compounds of Formula II'

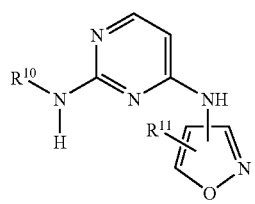

II' wherein $R^{10}$ is selected from phenyl, and 5–10 membered heterocyclyl; wherein $R^{10}$ is optionally substituted with 1–2 substituents selected from $R^{11}$;
preferably 3,4,5-trimethoxyphenyl, 3,4-dimethoxy-6-methylphenyl, 3-methoxy-4-morpholinylphenyl and 5-indazolyl;
wherein $R^{11}$ is selected from $C_1$–$C_4$ alkyl, $C_2$–$C_3$ alkenyl, $C_2$–$C_3$ alkynyl, $C_3$–$C_{10}$ cycloalkyl, $C_4$–$C_6$ cycloalkenyl, phenyl, 5–6 membered heterocyclyl, fluoro, chloro, $CF_3$, —$OC(O)R^{12}$, —$NR^{12}R^{12}$, —$COOR^{12}$, —$C(O)R^{12}$, —$C(O)NR^{12}R^{12}$, —$SO_2R^{12}$, —$SO_2NR^{12}R^{12}$, —$NR^{12}C(O)NR^{12}R^{12}$, —$NR^{12}C(O)R^{12}$, —$NR^{12}(COOR^{12})$, —$NR^{12}SO_2NR^{12}R^{12}$, —$NR^{12}SO_2R^{12}$, —$OC(O)NR^{12}R^{12}$, —$OR^{13}$, $C_1$–$C_3$ alkyl substituted with 1–3 substituents independently selected from optionally substituted phenyl and optionally substituted 5–6 membered heterocyclyl; and
$C_2$–$C_3$ alkenyl substituted with 1–3 substituents independently selected from optionally substituted phenyl and optionally substituted 5–6 membered heterocyclyl;
preferably cyclohexyl, adamantyl, phenyl and tert-butyl;
wherein $R^{12}$ is selected from H, $C_{1-6}$-alkyl, and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, $NO_2$, CN, $C_{1-4}$-alkylcarbonyl, $C_{1-4}$-alkylaminocarbonyl, aminocarbonyl, aminosulfonyl and acetyl; and
wherein $R^{13}$ is selected from H, $C_{1-6}$-alkyl, amino-$C_{1-6}$-alkyl, $C_{1-6}$-alkylamino-$C_{1-6}$-alkyl, aminocarbonyl-$C_{1-6}$-alkyl, $C_{1-6}$-alkylaminocarbonyl-$C_{1-6}$-alkyl, and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, $NO_2$, CN, $C_{1-4}$-alkylcarbonyl, $C_{1-4}$-alkylaminocarbonyl, aminocarbonyl, aminosulfonyl and acetyl;
and pharmaceutically acceptable salts thereof.
The invention also relates to compounds of Formula III'

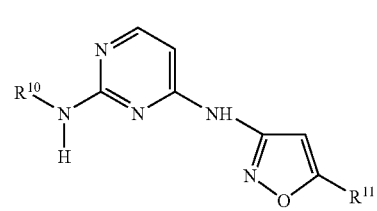

III' wherein $R^{10}$ is selected from phenyl, and 5–10 membered heterocyclyl; wherein $R^{10}$ is optionally substituted with 1–2 substituents selected from $R^{11}$;
preferably 3,4,5-trimethoxyphenyl, 3,4-dimethoxy-6-methylphenyl, 3-methoxy-4-morpholinylphenyl and 5-indazolyl;
wherein $R^{11}$ is selected from $C_1$–$C_4$ alkyl, $C_2$–$C_3$ alkenyl, $C_2$–$C_3$ alkynyl, $C_3$–$C_{10}$ cycloalkyl, $C_4$–$C_6$ cycloalkenyl, phenyl, 5–6 membered heterocyclyl, fluoro, chloro, $CF_3$, —$OC(O)R^{12}$, —$NR^{12}R^{12}$, —$COOR^{12}$, —$C(O)R^{12}$, —$C(O)NR^{12}R^{12}$, —$SO_2R^{12}$, —$SO_2NR^{12}R^{12}$, —$NR^{12}C(O)NR^{12}R^{12}$, —$NR^{12}C(O)R^{12}$, —$NR^{12}(COOR^{12})$, —$NR^{12}SO_2NR^{12}R^{12}$, —$NR^{12}SO_2R^{12}$, —$OC(O)NR^{12}R^{12}$, —$OR^{13}$, $C_1$–$C_3$ alkyl substituted with 1–3 substituents independently selected from optionally substituted phenyl and optionally substituted 5–6 membered heterocyclyl; and
$C_2$–$C_3$ alkenyl substituted with 1–3 substituents independently selected from optionally substituted phenyl and optionally substituted 5–6 membered heterocyclyl;
preferably cyclohexyl, adamantyl, phenyl and tert-butyl;

wherein $R^{12}$ is selected from H, $C_{1-6}$-alkyl, and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, $NO_2$, CN, $C_{1-4}$-alkylcarbonyl, $C_{1-4}$-alkylaminocarbonyl, aminocarbonyl, aminosulfonyl and acetyl; and wherein $R^{13}$ is selected from H, $C_{1-6}$-alkyl, amino-$C_{1-6}$-alkyl, $C_{1-6}$-alkylamino-$C_{1-6}$-alkyl, aminocarbonyl-$C_{1-6}$-alkyl, $C_{1-6}$-alkylaminocarbonyl-$C_{1-6}$-alkyl, and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, $NO_2$, CN, $C_{1-4}$-alkylcarbonyl, $C_{1-4}$-alkylaminocarbonyl, aminocarbonyl, aminosulfonyl and acetyl;

and pharmaceutically acceptable salts thereof.

The invention also relates to compounds of Formula IV

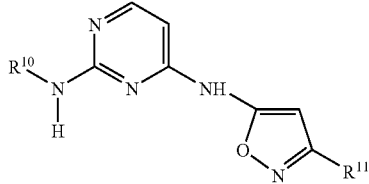

IV wherein $R^{10}$ is selected from phenyl, and 5–10 membered heterocyclyl; wherein $R^{10}$ is optionally substituted with 1–2 substituents selected from $R^{11}$;

preferably 3,4,5-trimethoxyphenyl, 3,4-dimethoxy-6-methylphenyl, 3-methoxy-4-morpholinylphenyl and 5-indazolyl;

wherein $R^{11}$ is selected from $C_1$–$C_4$ alkyl, $C_2$–$C_3$ alkenyl, $C_2$–$C_3$ alkynyl, $C_3$–$C_{10}$ cycloalkyl, $C_4$–$C_6$ cycloalkenyl, phenyl, 5–6 membered heterocyclyl, fluoro, chloro, $CF_3$, —OC(O)$R^{12}$, —NR$^{12}$R$^{12}$, —COOR$^{12}$, —C(O)R$^{12}$, —C(O)NR$^{12}$R$^{12}$, —SO$_2$R$^{12}$, —SO$_2$NR$^{12}$, —NR$^{12}$C(O)NR$^{12}$R$^{12}$, —NR$^{12}$C(O)R$^{12}$, —NR$^{12}$(COOR$^{12}$), —NR$^{12}$SO$_2$NR$^{12}$R$^{12}$, —NR$^{12}$SO$_2$R$^{12}$, —OC(O)NR$^{12}$R$^{12}$, —OR$^{13}$, $C_1$–$C_3$ alkyl substituted with 1–3 substituents independently selected from optionally substituted phenyl and optionally substituted 5–6 membered heterocyclyl; and $C_2$–$C_3$ alkenyl substituted with 1–3 substituents independently selected from optionally substituted phenyl and optionally substituted 5–6 membered heterocyclyl;

preferably cyclohexyl, adamantyl, phenyl and tert-butyl;

wherein $R^{12}$ is selected from H, $C_{1-6}$-alkyl, and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, $NO_2$, CN, $C_{1-4}$-alkylcarbonyl, $C_{1-4}$-alkylaminocarbonyl, aminocarbonyl, aminosulfonyl and acetyl; and wherein $R^{13}$ is selected from H, $C_{1-6}$-alkyl, amino-$C_{1-6}$-alkyl, $C_{1-6}$-alkylamino-$C_{1-6}$-alkyl, aminocarbonyl-$C_{1-6}$-alkyl, $C_{1-6}$-alkylaminocarbonyl-$C_{1-6}$-alkyl, and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, $NO_2$, CN, $C_{1-4}$-alkylcarbonyl, $C_{1-4}$-alkylaminocarbonyl, aminocarbonyl, aminosulfonyl and acetyl;

and pharmaceutically acceptable salts thereof.

A family of specific compounds of particular interest within Formula I consists of compounds and pharmaceutically-acceptable salts thereof as follows:

$N^4$-(5-tert-butylisoxazol-3-yl)-$N^2$-(4,5-dimethoxy-2-methyl-phenyl)-pyrimidine-2,4-diamine; and
$N^4$-(5-tert-butylisoxazol-3-yl)-$N^2$-(3,4,5-trimethoxy-phenyl)-pyrimidine-2,4-diamine.

A family of specific compounds of particular interest within Formula I consists of compounds and pharmaceutically-acceptable salts thereof as follows:

$N^4$-(5-tert-Butylisoxazol-3-yl)-$N^2$-(3,4,5-trimethoxy-phenyl)-pyrimidine-2,4-diamine;
$N^4$-(5-t-Butyl-isoxazol-3-yl)-$N^2$-(4,5-dimethoxy-2-methyl-phenyl)-pyrimidine-2,4-diamine;
$N^4$-(5-t-Butyl-isoxazol-3-yl)-$N^2$-(1H-indazol-5-yl)-pyrimidine-2,4-diamine;
$N^2$-(3-Methoxy-4-morpholin-4-yl-phenyl)-$N^4$-(5-phenyl-isoxazol-3-yl)-pyrimidine-2,4-diamine;
$N^2$-(3,4,5-trimethoxyphenyl)-$N^4$-(5-phenylisoxazol-3-yl)-2,4-pyrimidinediamine;
$N^2$-(2-methyl-4,5-dimethoxyphenyl)-$N^4$(5-phenylisoxazol-3-yl)-2,4-pyrimidinediamine;
$N^2$-(2-methyl-4,5-dimethoxyphenyl)-$N^4$-(5-adamantylisoxazol-3-yl)-2,4-pyrimidinediamine; and
$N^2$-(3,4,5-Trimethoxyphenyl)-$N^4$-(3-cyclohexylisoxazol-5-yl)-2,4-pyrimidinediamine.

Indications

Compounds of the present invention would be useful for, but not limited to, the prevention or treatment of cancer and related diseases. The compounds of the invention have kinase inhibitory activity, such as IGF-1R inhibitory activity. The compounds of the invention are useful in therapy as antineoplasia agents.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the present invention are also useful for promoting apoptosis.

The compounds of this invention may also act as inhibitors of other protein kinases, e.g. ErbB, KDR, CDK-2, LCK, CDK-5, IKK, JNK3, and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

Definitions

The term "prevention" includes either preventing the onset of disorders altogether or delaying the onset of a preclinically evident stage of disorders in individuals. This includes prophylactic treatment of those at risk of developing a disease, such as a cancer, for example. "Prophylaxis" is another term for prevention.

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by the ability to treat neoplasia.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The terms "ring" and "ring system" refer to a ring comprising the delineated number of atoms, said atoms being carbon or, where indicated, a heteroatom such as nitrogen, oxygen or sulfur. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

Leaving groups are species that may be detached from a molecule during a reaction and are known in the art. Examples of such groups include, but are not limited to, halogen groups (e.g., I, Br, F, Cl), sulfonate groups (e.g., mesylate, tosylate), sulfide groups (e.g., $SCH_3$), and the like. Nucleophiles are species that may be attached to a molecule during reaction and are known in the art. Examples of such groups include, but are not limited to, amines, Grignard reagents, anionic species (e.g., alkoxides, amides, carbanions) and the like.

The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 5 substituents such as lower alkyl, hydroxyl, halo, lower haloalkyl, nitro, cyano, lower alkoxy and lower alkylamino.

The term "heterocyclyl" embraces saturated, partially saturated and unsaturated heteroatom-containing ring-shaped radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic group containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

The term "sulfonyl", whether used alone or linked to other terms such as alkylsulfonyl, denotes respectively divalent radicals —SO$_2$—.

The term "alkylsulfonyl" embraces sulfonyl radicals substituted with an alkyl radical. More preferred alkylsulfonyl radicals are "lower alkylsulfonyl" radicals having one to six carbon atoms. Even more preferred are lower alkylsulfonyl radicals having one to three carbon atoms. Examples of such lower alkylsulfonyl radicals include methylsulfonyl, and ethylsulfonyl.

The terms "sulfamyl," "aminosulfonyl" and "sulfonamidyl," denotes a sulfonyl radical substituted with an amine radical, (—SO$_2$NH$_2$).

The terms "carboxy" or "carboxyl", whether used alone or with other terms, such as "carboxyalkyl", denotes —CO$_2$H.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "heterocyclylalkylenyl" embraces heterocyclyl-substituted alkyl radicals. Preferable heterocyclyl alkylenyl radicals are "lower heterocyclylalkylenyl" radicals having heterocyclyl radicals attached to alkyl radicals having one to six carbon atoms. More preferred are heterocyclyl-$C_1$–$C_2$-alkylenyl radicals such as morpholinylmethyl, methylpiperdinylmethyl, methylpiperazinylmethyl, and the like.

The term "carbonyl", whether used alone or with other terms, such as "aminocarbonyl", denotes —(C═O)—.

The term "alkylamino" embraces "N-alkylamino" and "N,N-dialkylamino" where amino groups are substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino or the like.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl, such as N-methylaminomethyl, N,N-dimethylaminoethyl, N,N-diethylaminomethyl and the like.

The term "cycloalkyl" includes saturated carbocyclic groups. Preferred cycloalkyl groups include $C_3$–$C_6$ rings. More preferred compounds include, cyclopentyl, cyclopropyl, and cyclohexyl.

The term "cycloalkenyl" includes carbocyclic groups have one or more carbon-carbon double bonds. "Cycloalkenyl" and "cycloalkyldienyl" compounds are included. Preferred cycloalkenyl groups include $C_3$–$C_6$ rings. More preferred compounds include, for example, cyclopentenyl, cyclopentadienyl, cyclohexenyl and cycloheptadienyl.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above. The aryl portion may be further substituted.

The term "heteroaryloxy" embraces optionally substituted heteroaryl radicals, as defined above, attached to an oxygen atom.

The term "heteroarylalkoxy" embraces heteroarylalkyl radicals attached through an oxygen atom. More preferred heteroarylalkoxy radicals are "lower heteroarylalkoxy" radicals having optionally substituted heteroarylalkyl radicals attached to lower alkoxy radical as described above.

The term "aminocarbonyl" denotes an amide group of the formula —C(=O)NH$_2$.

The term "alkoxycarbonyl" denotes an ester group, where a carbonyl radical is substituted with an alkoxy radical. More preferred are "lower alkoxycarbonyl" having lower alkoxy radicals as described above attached to a carbonyl radical.

The term "alkylcarbonyl" denotes carbonyl groups which have been substituted with an alkyl radical. More preferred are $C_1$–$C_6$-alkylcarbonyl radicals, such as methylcarbonyl, ethlcarbonyl and propylcarbonyl.

The terms "N-alkylaminocarbonyl" and "N,N-dialkylaminocarbonyl" denote aminocarbonyl radicals substituted with one or two alkyl radicals, respectively. More preferred are "lower alkylaminocarbonyl" having lower alkyl radicals as described above attached to an aminocarbonyl radical.

A "pharmaceutically acceptable prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulas described herein.

The term "comprising" is meant to be open ended, including the indicated component but not excluding other elements.

The phrase "Formula I–IV" includes subformulas such as I' and III'.

The present invention preferably includes compounds that selectively inhibit IGF-1R.

The present invention also comprises the use of a compound of the invention, or pharmaceutically acceptable derivative thereof, in the manufacture of a medicament for the treatment either acutely or chronically of an apoptosis mediated disease state, including those described previously. The compounds of the present invention are useful in the manufacture of an anti-cancer medicament. The compounds of the present invention are also useful in the manufacture of a medicament to attenuate or prevent disorders through inhibition of IGF-1R.

The present invention comprises a pharmaceutical composition comprising a therapeutically-effective amount of a compound of Formulas I–IV in association with a least one pharmaceutically-acceptable carrier, adjuvant or diluent.

The present invention also comprises a method of treating apoptosis related disorders, in a subject, the method comprising treating the subject having or susceptible to such disorder with a therapeutically-effective amount of a compound of the present invention.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B. cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), SU 6668 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The invention relates to inhibitors of enzymes that catalyze phosphoryl transfer and/or that bind ATP/GTP nucleotides, compositions comprising the inhibitors, and methods of using the inhibitors and inhibitor compositions. The inhibitors and compositions comprising them are useful for treating or modulating disease in which phosphoryl transferases, including kinases, may be involved, symptoms of such disease, or the effect of other physiological events mediated by phosphoryl transferases, including kinases. The invention also provides for methods of making the inhibitor compounds and methods for treating diseases in which one or Imore phosphoryl transferase, including kinase, activities is involved.

Alternatively, the present compounds may also be used in co-therapies with other anti-neoplastic agents, such as other kinase inhibitors including p38 inhibitors and CDK inhibitors, TNF inhibitors, metallomatrix proteases inhibitors (MMP), EGFR inhibitors such as Iressa, KDR inhibitors, COX-2 inhibitors including celecoxib, rofecoxib, parecoxib, valdecoxib, and etoricoxib, NSAID's, SOD mimics or $\alpha_v\beta_3$ inhibitors.

The present invention comprises a process for the preparation of a compound of Formula I–IV.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Compounds of the present invention can possess, in general, tautomeric forms, which are included in the family of compounds in Formula I–IV.

Also included in the family of compounds of Formula I–IV are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I–IV may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are acetic, adipic, algenic, anthranilic, ascorbic, aspartic, benzoic, benzenesulfonic, butyric, camphoric, camphorsulfonic, citric, cyclopentanepropionic, cyclohexylaminosulfonic, digluconic, dodecylsulfonic, ethanesulfonic, formic, fumaric, galactaric, galacturonic, glycolic, gluconic, glucuronic, glucoheptanoic, glutamic, glycerophosphonic, heptanoic, hexanoic, 4-hydroxybenzoic, 2-hydroxyethanesulfonic, β-hydroxybutyric, lactic, malic, maleic, mandelic, mesylic, methanesulfonic, nicotinic, 2-naphthalenesulfonic, oxalic, palmoic, pectinic, pivalic, persulfuric, 2-phenylpropionic, picric, pyruvic, propionic, phenylacetic, embonic (pamoic), cyclopentane proprionic, pantothenic, toluenesulfonic, salicylic, sulfanilic, stearic, succinic, tartaric, thiocyanic, and undecanoic.

Suitable pharmaceutically-acceptable base addition salts of compounds of Formula I–IV include metallic salts, such as salts made from alkali metals and alkaline earth metals including, for example, aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, ammonia, triethylamine, trimethylamine. All of these salts may be prepared by conventional means from the corresponding compound of the invention by reacting, for example, the appropriate acid or base with the compound of Formula I–IV.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66, 1 (1977).

Combinations of substituents and variables envisioned by this invention are only those that result in the formation of stable compounds. The term "stable", as used herein, refers to compounds which possess stability sufficient to allow preparation.

As used herein, the compounds of this invention, including the compounds described herein, are defined to include pharmaceutically acceptable derivatives or prodrugs thereof.

Pharmaceutically acceptable salts of the compounds of this invention include those derived from pharmaceutically acceptable inorganic and organic acids and bases. Other acids, such as oxalic, while not in themselves pharmaceutically acceptable, may be employed in the preparation of salts useful as intermediates in obtaining the compounds of the invention and their pharmaceutically acceptable acid addition salts. This invention also envisions the quaternization of any basic nitrogen-containing groups of the compounds disclosed herein. Water or oil-soluble or dispersible products may be obtained by such quaternization.

The invention relates to a process for making a compound of any of the formulas described herein, comprising reacting a pyrimidine of one or more of the formulas:

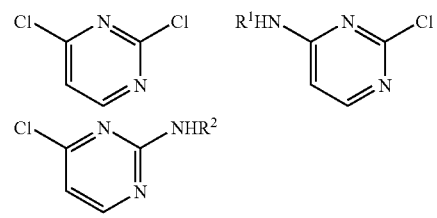

with an appropriate nucleophilic agent or agents, wherein the groups in said formulas are as defined herein.

The invention also relates to a process for making a compound of any of the formulas described herein, comprising reacting a pyrimidine of one or more of the formulas:

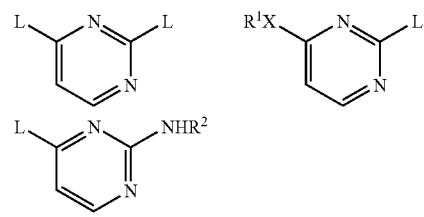

with an appropriate nucleophilic agent or agents, wherein L is defined as a leaving group and the groups in said formulas are as defined herein.

General Synthetic Procedures

The compounds of the invention can be synthesized according to the following procedures of Schemes 1–2, wherein the substituents are as defined for Formulas I–IV, above, except where further noted.

Scheme 1

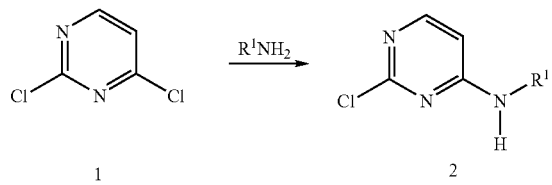

Monoamine substituted pyrimidines 2 can be prepared according to the method set out in Scheme 1. 2,4-Dichloropyrimidine 1 is coupled with heteroarylamines, in the presence of base, such as NaH, and a solvent, such as DMF or THF, at a temperature of about 0° C. to about RT to give (2-chloro-pyrimidin-4-yl)amine 2.

Alternatively, 2,4-dichloropyrimidine 1 is coupled with an amine in the presence of NaOt-Bu, in a solvent, such as t-BuOH, at a temperature about RT to yield monoamine-substituted pyrimidines 2.

Scheme 2

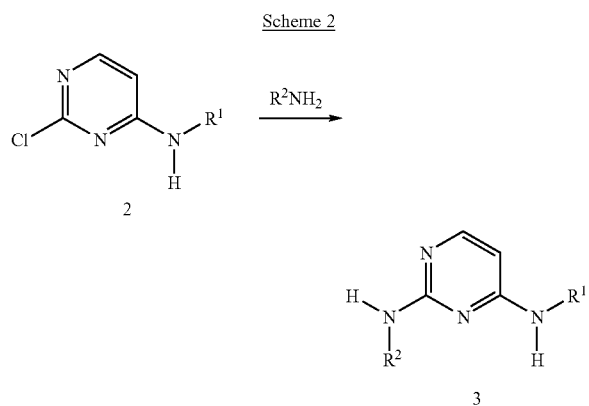

Monoamine substituted pyrimidines 2 are reacted with an amine having an active hydrogen, such as R²NH₂, in solvent, such as acetone and water, and in the presence of acid, such as conc. HCl, to give the diamine substituted pyrimidine 3.

Alternatively, the reaction can be performed in a solvent such as IPA or DMSO, with or without DIEA or in a solvent such as IPA or DMSO with or without Et₃N•TFA, or in a solvent such as HOAc.

Preferably the reaction is heated, more preferably at a temperature of about >50° C., even more preferably at a temperature of about 90–100° C.

If one or more other functional groups, for example carboxy, hydroxy, amino, or mercapto, are or need to be protected in a compound of Formulas I–IV, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (Methods of organic chemistry), Houben Weyl, 4th edition, Volume 15/1, Georg Thieme Verlag, Stuttgart 1974, in H.-D. Jakubke and H. Jescheit, "Aminosauren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide und Derivate" (Chemistry of carbohydrates: monosaccharides and derivatives), Georg Thieme Verlag, Stuttgart 1974.

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of formula I with a salt-forming group may be prepared in a manner known per se. Acid addition salts of compounds of formula I may thus be obtained by treatment with an acid or with a suitable anion exchange reagent. A salt with two acid molecules (for example a dihalogenide of a compound of formula I) may also be converted into a salt with one acid molecule per compound (for example a monohalogenide); this may be done by heating to a melt, or for example by heating as a solid under a high vacuum at elevated temperature, for example from 130–170° C., one molecule of the acid being expelled per molecule of a compound of formula I.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H⁺ form, depending on the type of reaction and/or reactants at reduced, normal, or elevated temperature, for example in the range from about –100° C. to about 190° C., preferably from about –80° C. to about 150° C., for example at about –80 to about 60° C., at RT, at about –20 to about 40° C. or at the boiling point of the solvent used, under atmospheric pressure or in a closed vessel, where appropriate under pressure, and/or in an inert atmosphere, for example, under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include, for example, H₂O, esters, typically lower alkyl-lower alkanoates, e.g. EtOAc, ethers, typically aliphatic ethers, e.g. Et₂O, or cyclic ethers, e.g. THF, liquid aromatic hydrocarbons, typically benzene or toluene, alcohols, typically MeOH, EtOH or 1-propanol, IPA, nitrites, typically CH₃CN, halogenated hydrocarbons, typically CH₂Cl₂, acid amides, typically DMF, bases, typically heterocyclic nitrogen bases, e.g. pyridine, carboxylic acids, typically lower alkanecarboxylic acids, e.g. HOAc, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of formula I–IV, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

The following examples contain detailed descriptions of the methods of preparation of compounds of Formulas I–IV. These detailed descriptions fall within the scope, and serve to exemplify, the above described General Synthetic Procedures which form part of the invention. These detailed descriptions are presented for illustrative purposes only and are not intended as a restriction on the scope of the invention.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention. The compounds of this invention may also be represented in multiple tautomeric forms, for example, as illustrated below:

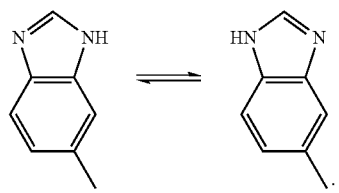

The invention expressly includes all tautomeric forms of the compounds described herein. The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Unless otherwise noted, all materials were obtained from commercial suppliers and used without further purification. All parts are by weight and temperatures are in Degrees centigrade unless otherwise indicated. All compounds showed NMR spectra consistent with their assigned structures.

In order that the invention described herein may be more readily understood, the following examples are set forth. It should be understood that these examples are for illustrative purposes only and are not to be construed as limiting this invention in any manner.

Analytical Methods:

Unless otherwise indicated all HPLC analyses were run on an HP-1000 or HP-1050 system with an HP Zorbax SB—$C_{18}$ (5μ) reverse phase column (4.6×150 mm) run at 30° C. with a flow rate of 1.00 mL/min. The mobile phase used solvent A ($H_2O$/0.1% TFA) and solvent B ($CH_3CN$/0.1% TFA) with a 20 min gradient from 10% to 90% $CH_3CN$. The gradient was followed by a 2 min return to 10% $CH_3CN$ and a 3 min flush. The peaks of interest eluted on the LC profiles at the times indicated.

LC-MS Methods:

Method A:
1. Samples were run on an HP-1100 system with an HP Zorbax SB—$C_8$ (5μ) reverse phase column (4.6×50 mm) run at 30° C. with a flow rate of 0.75 mL/min.
2. The mobile phase used solvent A ($H_2O$/0.1% AcOH) and solvent B ($CH_3CN$/0.1% AcOH) with a 10 min gradient from 10% to 90% $CH_3CN$. The gradient was followed by a 1 min return to 10% $CH_3CN$ and a 2 min flush.
3. The peaks of interest eluted on the LC profiles at the times indicated.

Method B:
4. Samples were run on an HP-1100 system with an HP Zorbax SB—$C_8$ (5μ) reverse phase column (4.6×50 mm) run at 30° C. with a flow rate of 1.5 mL/min.
5. The mobile phase used solvent A ($H_2O$/0.1% AcOH) and solvent B ($CH_3CN$/0.1% AcOH) with a 5 min gradient from 10% to 90% $CH_3CN$. The gradient was followed by a 0.5 min return to 10% $CH_3CN$ and a 1.5 min flush.

Preparative HPLC: Where indicated compounds of interest were purified via preparative HPLC using a Gilson workstation with a 30×100 mm column at 30 mL/min. The mobile phase used solvent A ($H_2O$/0.1% TFA) and solvent B ($CH_3CN$/0.1% TFA) with a 15 min gradient from 5% to 100% $CH_3CN$. The gradient was followed by a 2 min return to 5% $CH_3CN$.

Proton NMR Spectra:

Unless otherwise indicated all $^1H$ NMR spectra were run on an Varian series Mercury 300 or 400 MHz instrument. All observed protons are reported as parts per million (ppm) downfield from tetramethylsilane (TMS) or other internal reference in the appropriate solvent indicated.

The following abbreviations are used:

| | |
|---|---|
| AcOH, HOAc | acetic acid |
| $CH_3CN$ | acetonitrile |
| ATP | adenosine triphosphate |
| $NH_4Cl$ | ammonium chloride |
| $NH_4OH$ | ammonium hydroxide |
| BINAP | 2,2'-bis(diphenylphosphino)-1,1'binaphthyl |
| $BH_3$ | borane |
| BSA | bovine serum albumin |
| DDQ | 2,3-dichloro-5,6-dicyano-1,4-benzoquinone |
| $CH_2Cl_2$ | dichloromethane |
| DIEA | diisopropylethylamine |
| DIAD | diisopropyl azodicarboxylate |
| EDC | 1-(3-dimethylaminopropyl)-3-ethylcarbodiimide hydrochloride |
| DMF | dimethylformamide |
| DMSO | dimethyl sulfoxide |
| DPPA | diphenylphosporyl azide |
| DTT | dithiothreitol |
| EtOH | ethanol |
| EtOAc | ethyl acetate |
| $Et_2O$ | ethyl ether |
| $FeSO_4$ | ferric sulfate |
| g | gram |
| h | hour |
| HBr | hydrobromic acid |
| HCl | hydrochloric acid |
| $H_2$ | hydrogen |
| HOBt | hydroxybenzotriazole |
| IPA | isopropanol |
| LAH | lithium aluminum hydride |
| LiOH | lithium hydroxide |
| $MgSO_4$ | magnesium sulfate |
| $MnCl_2$ | manganese chloride |
| MeOH | methanol |
| MeI | methyl iodide |
| mg | milligram |
| mL | milliliter |
| min | minutes |
| $N_2$ | nitrogen |
| Pd/C | palladium on carbon |
| $Pd(OAc)_2$ | palladium acetate |
| $Pd(PPh_3)_4$ | palladium tetrakis triphenylphosphine |
| $Pd_2(dba)_3$ | tris(dibenzylideneacetone)di-palladium |
| $POCl_3$ | phosphoryl chloride |
| $PCl_5$ | phosphorous pentachloride |
| $P_2O_5$ | phosphorous pentoxide |
| Pt/C | platinum on carbon |
| $K_2CO_3$ | potassium carbonate |
| KOt-Bu | potassium t-butoxide |
| RT | Room temperature |
| $NaHCO_3$ | sodium bicarbonate |
| $Na_2CO_3$ | sodium carbonate |
| NaCl | sodium chloride |
| NaCN | sodium cyanide |
| $NaCNBH_3$ | sodium cyanoborohydride |
| NaH | sodium hydride |
| NaOH | sodium hydroxide |
| $Na_2SO_4$ | sodium sulfate |
| NaOt—Bu | sodium t-butoxide |
| t-BuOH | tert-butyl alcohol |
| t-BuOMe, MTBE | tert-butylmethylether |
| Boc | tert-butyloxycarbonyl |
| THF | tetrahydrofuran |
| TEA, $Et_3N$ | triethylamine |
| TFA | trifluoroacetic acid |
| $PPh_3$ | triphenyl phosphine |
| $H_2O$ | water |

EXAMPLE 1

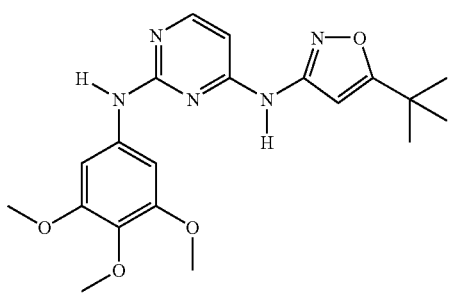

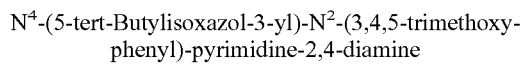

$N^4$-(5-tert-Butylisoxazol-3-yl)-$N^2$-(3,4,5-trimethoxyphenyl)-pyrimidine-2,4-diamine Step A To a solution of 3-amino-5-t-butylisoxazole (922 mg 6.58 mmol) in 15 mL of DMF at 0° C. was added 268 mg (6.71 mmol) of NaH (60% dispersion in mineral oil) in 4 portions over 1 min. The resulting mixture was stirred at 0° C. for 30 min when 1.0 g (6.71 mmol) of 2,3-dichloropyrimidine was added in 1 portion. The resulting mixture was warmed to RT (ice melt in dewar) and was stirred at RT for 22 h. The reaction mixture was quenched with saturated aqueous NH$_4$Cl and diluted with H$_2$O and EtOAc. The organic layer was washed 1× with brine. The combined aqueous layer and brine wash were extracted 1× with EtOAc. The combined organics were dried over Na$_2$SO$_4$, concentrated and purified by flash chromatography (elution with 2/1 hexanes/EtOAc) to give (2-chloro-pyrimidin-4-yl)-(5-tert-butyl-isoxazol-3-yl)-amine as a yellowish white solid.

Step B

A mixture of (2-chloropyrimidin-4-yl)-(5-tert-butyl-isoxazol-3-yl)amine (50 mg 0.198 mmol Step A) and 3,4,5-trimethoxyaniline (36.2 mg 0.198 mmol) was suspended in 0.15 mL of a 2M solution of Et$_3$N-TFA in DMSO (stock solution prepared by combining 1.28 g of Et$_3$N-TFA and 3 mL of DMSO) in a sealed tube. The resulting mixture was heated at 100° C. for 4 h, cooled to RT, diluted with CH$_2$Cl$_2$ (attempted crystallization), concentrated and purified via preparative HPLC to give N$^4$-(5-tert-butylisoxazol-3-yl)-N$^2$-(3,4,5-trimethoxy-phenyl)-pyrimidine-2,4-diamine as a green-gray amorphous solid. MS m/z=400. Calc'd for C$_{20}$H$_{25}$N$_5$O$_4$— 399.19.

EXAMPLE 2

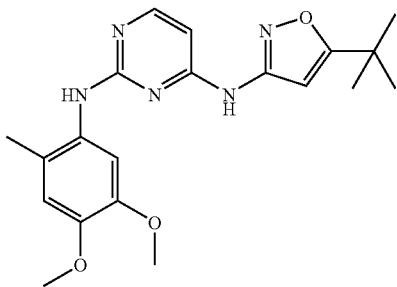

N$^4$(5-t-Butyl-isoxazol-3-yl)-N$^2$-(4,5-dimethoxy-2-methyl-phenyl)-pyrimidine-2,4-diamine Step A: Preparation of (5-t-Butyl-isoxazol-3-yl)-(2-chloro-pyrimidin-4-yl)-amine To a solution of 5-t-butyl-isoxazol-3-ylamine (10.0 g, 71.33 mmol) in t-BuOH (500 mL) at 20° C. was added NaOt-Bu (17.1 g, 178.3 mmol) in 3 portions over 10 min. The solution turned pale yellow with the appearance of a thick, white precipitate. The mixture was stirred at 20° C. for 1 h, then 2,4-dichloropyrimidine (15.9 g, 107.0 mmol) was added. The mixture was stirred for an additional 90 min. at 20° C., accompanied by the dissolution of the white precipitate and appearance of an orange color. NH$_4$Cl (aq., sat., 100 mL) and H$_2$O (1 L) were added, and the mixture was extracted with CH$_2$Cl$_2$ (3×200 mL). The combined organic layers were washed with H$_2$O (300 mL), brine, and dried with MgSO$_4$ before being filtered and concentrated under reduced pressure. Purification by chromatography of the crude reaction mixture (96:4 CH$_2$Cl$_2$:MeOH) provided the title compound.

Step B: Preparation of N$^4$-(5-t-Butyl-isoxazol-3-yl)-N$^2$-(4,5-dimethoxy-2-methyl-phenyl)-pyrimidine-2,4-diamine To a slurry of (5-L-butyl-isoxazol-3-yl)-(2-chloro-pyrimidin-4-yl)-amine (0.110 g, 0.435 mmol, Step A) in DMSO (0.110 mL) was added 2-methyl-4,5-dimethoxyaniline (0.073 g, 0.435 mmol). The mixture was heated in a sealed tube at 110° C. for 90 min until TLC indicated the disappearance of starting materials. The mixture was taken up in CH$_2$Cl$_2$ (5 mL) followed by the addition of NaHCO$_3$ (aq., sat. 1 mL) and H$_2$O (5 mL). Extraction with CH$_2$Cl$_2$ (5×5 mL), followed by drying with MgSO$_4$ and filtration yielded a crude mixture that was concentrated under reduced pressure. Purification by chromatography (97:3 CH$_2$Cl$_2$:MeOH) on silica gel afforded the title compound as a purple solid. MS m/z=384.2. Calc'd for C$_{20}$H$_{25}$N$_5$O$_3$: 383.45.

The following Examples were prepared from the corresponding amines in a manner similar to that described above for Example 2:

EXAMPLE 3

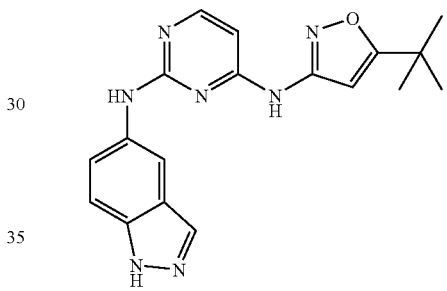

N$^4$-(5-t-Butyl-isoxazol-3-yl)-N$^2$-(1H-indazol-5-yl)-pyrimidine-2,4-diamine

MS m/z=350.3. Calc'd for C$_{18}$H$_{19}$N$_7$O: 349.40.

EXAMPLE 4

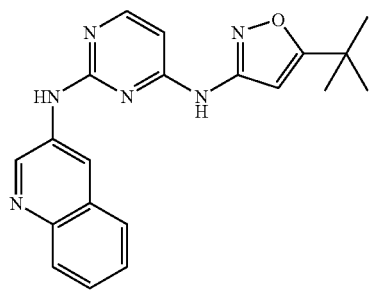

N$^4$-(5-t-Butyl-isoxazol-3-yl)-N$^2$-quinolin-3-yl-pyrimidine-2,4-diamine

MS m/z=361.3. Calc'd for C$_{20}$H$_{20}$N$_6$O: 360.42.

EXAMPLE 5

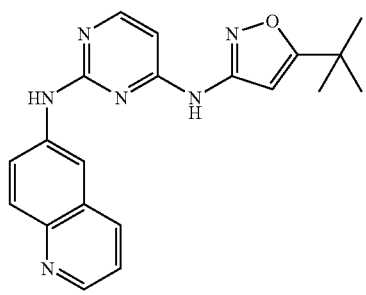

$N^4$-(5-t-Butyl-isoxazol-3-yl)-$N^2$-quinolin-6-yl-pyrimidine-2,4-diamine

MS m/z=361.3. Calc'd for $C_{20}H_{20}N_6O$: 360.42.

EXAMPLE 6

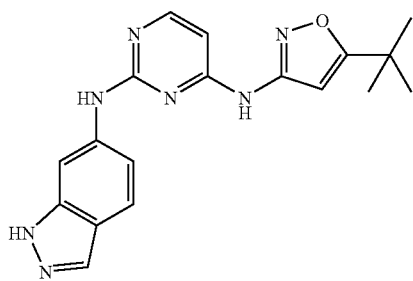

$N^4$-(5-t-Butyl-isoxazol-3-yl)-$N^2$-(1H-indazol-6-yl)-pyrimidine-2,4-diamine

MS m/z=350.3. Calc'd for $C_{18}H_{19}N_7O$: 349.40.

EXAMPLE 7

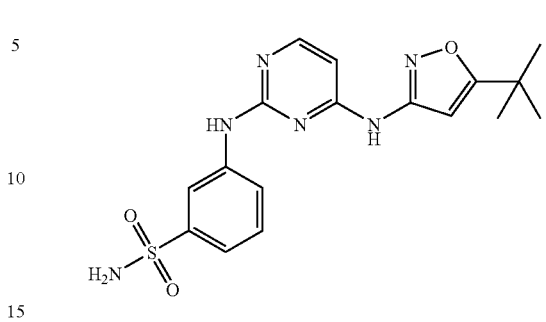

3-[4-(5-t-Butyl-isoxazol-3-ylamino)-pyrimidin-2-ylamino]-benzenesulfonamide

To a slurry of (5-t-butyl-isoxazol-3-yl)-(2-chloro-pyrimidin-4-yl)-amine (Example 2, Step A) (0.120 mg, 0.47 mmol) in DMSO (0.120 mL) was added 3-aminobenzenesulfonamide (0.082 g, 0.47 mmol). The reaction mixture was heated at 120° C. in a sealed tube for 1 h at which time TLC indicated the disappearance of starting material. IPA (5 mL) was added and the mixture was filtered and washed with IPA (2×1 mL) to yield the title compound as a white solid.

MS m/z=389.3. Calc'd for $C_{17}H_{20}N_6O_3S$: 388.45.

EXAMPLES 8–13

Examples 8–13 were prepared from the corresponding amines in a manner similar to that described above for Example 7.

| Example | Structure | Mass Calc'd | Mass Obs. |
|---|---|---|---|
| 8 | 4-[4-(5-t-Butyl-isoxazol-3ylamino)-pyrimidin-2-ylamino]-benzensulfonamide | $C_{17}H_{20}N_6O_3S$: 388.45 | 389.3 |

| Example | Structure | Mass Calc'd | Mass Obs. |
|---|---|---|---|
| 9 | N⁴-(5-t-Butyl-isoxazol-3-yl)-N²-(3-chloro-phenyl)-pyrimidine-2,4-diamine | $C_{17}H_{18}ClN_5O$: 343.82 | 344.2 |
| 10 | N-{3-[4-(5-t-Butyl-isoxazol-3-ylamino)-pyrimidin-2-ylamino]-phenyl}-acetamide | $C_{19}H_{22}N_6O_2$: 366.43 | 367.4 |
| 11 | N-{4-[4-(5-t-Butyl-isoxazol-3-ylamino)-pyrimidin-2-ylamino]-phenyl}-N-methyl-acetamide | $C_{20}H_{24}N_6O_2$: 380.45 | 381.4 |
| 12 | N-Acetyl-4-[4-(5-t-butyl-isoxazol-3-ylamino)-pyrimidin-2-ylamino]-benzenesulfonamide | $C_{19}H_{22}N_6O_4S$: 430.49 | 431.4 |

| Example | Structure | Mass Calc'd | Mass Obs. |
|---|---|---|---|
| 13 | N⁴-(5-t-Butyl-isoxazol-3-yl)-N²-(3-isopropyl-phenyl)-pyrimidine-2,4-diamine | $C_{20}H_{25}N_5O$: 315.46 | 352.3 |

EXAMPLE 14

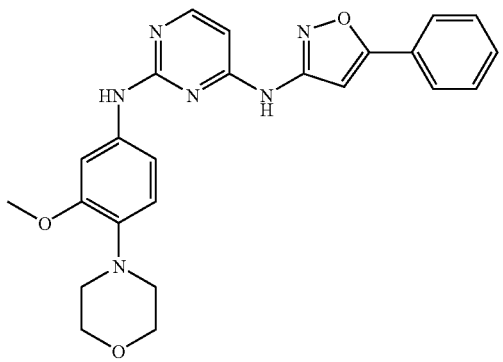

$N^2$-(3-Methoxy-4-morpholin-4-yl-phenyl)-$N^4$-(5-phenyl-isoxazol-3-yl)-pyrimidine-2,4-diamine Step A: Preparation of (2-Chloro-pyrimidin-4-yl)-(5-phenyl-isoxazol-3-yl)-amine The title compound was prepared in a manner similar to the method described in Example 2 (Step A) using the appropriate isoxazole reagent.

Step B: Preparation of 4-(2-Methoxy-4-nitro-phenyl)-morpholine

To a mixture of 1-bromo-2-methoxy-4-nitro-benzene (2.5 g, 10.8 mmol), $Pd_2(dba)_3$ (0.124 g, 0.215 mmol), NaOt-Bu (1.55 g, 16.2 mmol) and BINAP (0.202 g, 0.323 mmol) in toluene (20 mL) at 20° C. was added morpholine (1.5 mL, 17.2 mmol) over 10 min. The mixture was stirred at 80° C. for 3 h when TLC indicated no starting material remained, at which time the mixture was evaporated under reduced pressure followed by the addition of $H_2O$ (50 mL). $CH_2Cl_2$ extraction (3×15 mL), followed by drying of the combined organic layers with $MgSO_4$ afforded, after filtration and concentration, an orange oil. Chromatography on silica gel (97:3 $CH_2Cl_2$/MeOH) yielded pure compound.

Step C: Preparation of 3-Methoxy-4-morpholin-4-yl-phenylamine

To a solution of 4-(2-methoxy-4-nitro-phenyl)-morpholine (1.0 g, 4.2 mmol, Step B) in EtOH (25 mL) at 20 ° C was added Pd/C (100 mg). The flask was capped with a rubber septum and $H_2$ pressure was applied through a balloon/needle. The reaction mixture was stirred at 20° C. for 12 h, filtered through sand/Celite® and concentrated. Purification by chromatography of the crude mixture (97:3 $CH_2Cl_2$:MeOH) afforded 3-methoxy-4-morpholin-4-yl-phenylamine as a purple solid.

Step D: Preparation of $N^2$-(3-Methoxy-4-morpholin-4-yl-phenyl)-$N^4$-(5-phenyl-isoxazol-3-yl)-pyrimidine-2,4-diamine The title compound was prepared by the method described in Example 2, Step B using 3-methoxy-4-morpholin-4-yl-phenylamine (Step C). MS m/z=445.3. Calc'd for $C_{24}H_{24}N_6O_3$: 444.50.

EXAMPLE 15

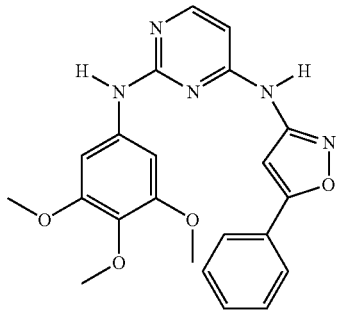

$N^2$-(3,4,5-Trimethoxyphenyl)-$N^4$-(5-phenylisoxazol-3-yl)-2,4-pyrimidinediamine Step A n-Butyllithium (21.6 mL, 2.5M in hexane) was added dropwise to a solution of phenylacetylene (5 g, 0.05 mol) in dry Et$_2$O (200 mL) maintaining at −78° C. under inert atmosphere. A solution of 2-pyridyl cyanate (7.2 g, 0.06 mol) in dry Et$_2$O (100 mL) was added dropwise keeping the temperature below −60° C. The mixture was stirred for 30 min at −78° C. then warmed to RT. The reaction was diluted with Et$_2$O and quenched with 1N NaOH. The organic layer was washed once with 1N HCl and once with saturated NaHCO$_3$. The solvent was removed under vacuum maintaining the temperature under 30° C. to give 3-phenyl-2-propynenitrile as a colorless crystalline solid.

Step B

To a stirred solution of 3-phenyl-2-propyne-nitrile (1.27 g, 0.01 mol, Step A) in EtOH (20 mL) was added at RT hydroxylamine hydrochloride (3.5 g, 0.05 mol) followed by 10% NaOH (28 mL). The exothermic reaction was stirred at RT 24 h, then diluted with H$_2$O. The resulting precipitate was filtered off, washed with H$_2$O and dried over P2O$_5$ to afford 3-amino-5-phenylisoxazole as a white crystalline solid.

Step C

To a stirred suspension of 3-amino-5-phenylisoxazole (160 mg, 1 mmol, Step B) in t-BuOH (5 mL) was added NaOt-Bu (240 mg,). The mixture (slurry) was stirred at RT for 1 h. Subsequently, 2,4-dichloro-1,3-pyrimidine (223 mg, 1.5 mmol) was added portion-wise and the reaction was stirred an additional 2 h. The reaction was quenched by addition of a saturated aqueous solution of NH$_4$Cl, and extracted with CH$_2$Cl$_2$. The extract was dried over MgSO$_4$ and evaporated. The crude mixture was purified by flash chromatography using 20% EtOAc/Hexane as eluant to provide 2-chloro-N$^4$-(5-phenylisoxazol-3-yl)-4-pyrimidineamine as a white solid.

Step D

The title compound was prepared by the method described in Example 1 using 2-chloro-N$^4$-(5-phenylisoxazol-3-yl)-4-pyrimidineamine and 3,4,5-trimethoxyaniline. MS (MH$^+$)=420.4, Calc'd for C$_{22}$H$_{21}$N$_5$O$_4$— 419.44.

EXAMPLE 16

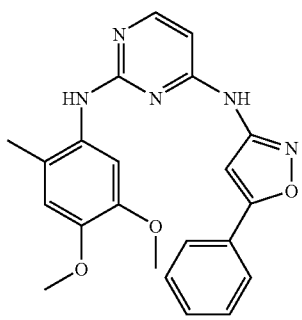

N$^2$-(2-methyl-4,5-dimethoxyphenyl)-N$^4$-(5-phenyl-isoxazol-3-yl)-2,4-pyrimidinediamine The title compound was prepared by the method described in Example 1 using 2-chloro-N$^4$-(5-phenylisoxazol-3-yl)-4-pyrimidineamine and 2-methyl-4,5-dimethoxyaniline.
MS (MH$^+$)=404.7; Calc'd for C$_{22}$H$_{21}$N$_5$O$_3$— 403.44.

EXAMPLE 17

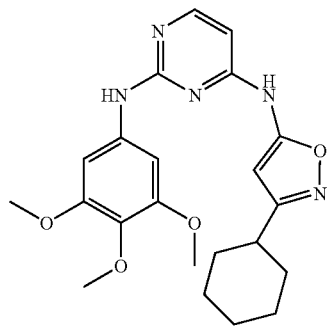

N$^2$-(3,4,5-Trimethoxyphenyl)-N$^4$-(3-cyclohexylisoxazol-5-yl)-2,4-pyrimidinediamine Step A To 700 mL of THF cooled at −78° C. under inert atmosphere was added n-butyllithium (56 mL, 2.5 M in hexane) followed by CH$_3$CN (7.3 mL, 0.14 mol) maintaining the temperature below −70° C. The mixture was stirred at −78° C. for 20 min then a solution of methyl cyclohexane carboxylate (10 g, 0.07 mol) in dry THF (300 mL) was added dropwise, maintaining the temperature under −60° C. The reaction was stirred an additional 20 min at −78° C., warmed to −20° C. and quenched by addition of saturated aq. NH$_4$Cl. The reaction mixture was diluted with H$_2$O and extracted with t-BuOMe. The solvents were removed under vacuum to give 3-cyclohexyl-3-oxopropanenitrile as a colorless oil.

Step B

To a stirred solution of 3-cyclohexyl-3-oxopropanenitrile (1 g, 6.6 mmol, Step A) in EtOH (1 mL) at RT was added hydroxylamine (0.81 mL, 50% in H$_2$O). The reaction was stirred 12 h at RT. The solid was filtered off, washed with 1N NaOH, then H$_2$O and dried over P$_2$O$_5$ to give 5-amino-3-cyclohexylisoxazole.

Step C

The 5-amino-3-cyclohexylisoxazole (Step B) was coupled to the 2,4-dichloropyridine using the general procedure described in Example 16 (step C) to afford 2-chloro-N$^4$-(5-amino-3-cyclohexylisoxazolyl)-2,4-pyrimidineamine as an off white solid.

Step D

The title compound was prepared by the method described in Example 1 using 2-chloro-N$^4$-(3-cyclohexyl-isoxazol-5-yl)-4-pyrimidineamine (Step C) and 3,4,5-trimethoxyaniline. MS (MH$^+$)=426.5; Calc'd for C$_{22}$H$_{27}$N$_5$O$_4$— 425.49.

EXAMPLE 18

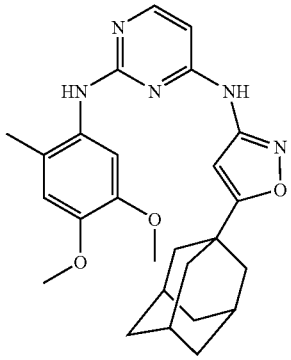

N²-(4,5-Dimethoxy-2-methylphenyl)-N⁴-(5-adamantylisoxazol-3-yl)-2,4-pyrimidinediamine The title compound was prepared by the method described in Example 1 using 2-chloro-N⁴-(5-adamantylisoxazol-3-yl)-4-pyrimidineamine and 2-methyl-4,5-dimethoxyaniline. MS (MH⁺)=462.2; Calc'd for $C_{26}H_{31}N_5O_3$— 461.57.

Other compounds included in this invention are set forth in Tables 1–2 below.

TABLE 1

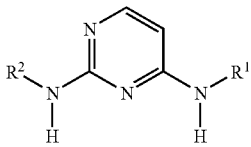

| # | R² | R¹ |
|---|---|---|
| 19. | 1-benzylindazol-5-yl | 5-tert-butyl-3-isoxazolyl |
| 20. | 1-benzylindazol-5-yl | 5-tert-butyl-3-isothiazolyl |
| 21. | naphth-1-yl | 5-tert-butyl-2-oxazolyl |
| 22. | 4-benzyloxy-phenyl | 5-tert-butyl-2-thiazolyl |
| 23. | 4-benzyloxy-3-chlorophenyl | 4-tert-butyl-2-thiazolyl |
| 24. | 3-chloro-4-fluorophenyl | 4-tert-butyl-2-oxazolyl |
| 25. | 3-chloronaphth-1-yl | 5-tert-butyl-1,3,4-oxadiazol-2-yl |
| 26. | 4-methoxycarbonylphenyl | 5-tert-butyl-1,3,4-thiadiazol-2-yl |
| 27. | 3-(2-methoxyethoxy)-4-methoxyphenyl | 5-tert-butyl-1,2,4-oxadiazol-2-yl |
| 28. | 3,4-dimethoxyphenyl | 5-tert-butyl-1,2,4-thiadiazol-2-yl |
| 29. | 3,4-diethoxyphenyl | 2-tert-butyl-5-oxazolyl |
| 30. | 3-bromophenyl | 2-tert-butyl-5-thiazolyl |
| 31. | 3-methoxy-4-(2-methoxyethoxy)phenyl | 2-tert-butyl-4-thiazolyl |
| 32. | 3-methylphenyl | 2-tert-butyl-4-oxazolyl |
| 33. | 4,5-dimethoxy-3-(2-morpholin-4-yl-ethoxy)phenyl | 5-tert-butyl-1,3,4-oxadiazol-2-yl |
| 34. | 3-aminocarbonylphenyl | 5-tert-butyl-1,2,4-oxadiazol-2-yl |
| 35. | 3-CH₃OCOCH₂-phenyl | 5-tert-butyl-1,3,4-thiadiazol-2-yl |
| 36. | 3-(4-nitrophenylsulfonylamino)phenyl | 5-tert-butyl-1,3,4-thiadiazol-2-yl |
| 37. | 5-chloro-2-methyl-phenyl | 5-tert-butyl-3-isoxazolyl |
| 38. | 4-[HO(CH₂)O]phenyl | 5-tert-butyl-3-isothiazolyl |
| 39. | 6-indazolyl | 2-tert-butyl-4-thiazolyl |
| 40. | 5-benzimidazolyl | 2-tert-butyl-4-oxazolyl |
| 41. | 3,4-dimethoxy-6-methylphenyl | 5-tert-butyl-3-isothiazolyl |

TABLE 2

| # | R² | R³ |
|---|---|---|
| 42. | 3-quinolyl | tert-butyl |
| 43. | 6-quinolyl | tert-butyl |
| 44. | 2,5-dimethoxyphenyl | tert-butyl |
| 45. | 2-chloro-5-methoxyphenyl | tert-butyl |
| 46. | 4-methoxy-2-methylphenyl | tert-butyl |
| 47. | 5-methoxy-2-methylphenyl | tert-butyl |
| 48. | 3-trifluoromethoxyphenyl | tert-butyl |
| 49. | 3-(1,1,2,2-tetrafluoroethoxy)phenyl | tert-butyl |
| 50. | 4-trifluoromethoxyphenyl | tert-butyl |
| 51. | 6-indazolyl | tert-butyl |
| 52. | 5-benzimidazolyl | tert-butyl |
| 53. | 1-methyl-5-indazolyl | isopropyl |
| 54. | 2-methyl-2H-indazol-5-yl | tert-butyl |
| 55. | 3-isopropylphenyl | tert-butyl |
| 56. | 3,5-dimethoxyphenyl | tert-butyl |
| 57. | 3,4-dimethoxyphenyl | tert-butyl |
| 58. | 1-methoxy-3-naphthyl | tert-butyl |
| 59. | 1,3-benzodioxol-5-yl | tert-butyl |
| 60. | 2-methoxyphenyl | isopropyl |
| 61. | 2-methoxyphenyl | tert-butyl |
| 62. | 3-methoxyphenyl | tert-butyl |
| 63. | 4-methoxyphenyl | tert-butyl |
| 64. | 3,4-diethoxyphenyl | tert-butyl |
| 65. | 3,5-bis(trifluoromethyl)phenyl | tert-butyl |
| 66. | 3-fluoro-5-(trifluoromethyl)phenyl | tert-butyl |
| 67. | 3-ethylphenyl | tert-butyl |
| 68. | 4-ethylphenyl | tert-butyl |
| 69. | 3-ethynylphenyl | tert-butyl |
| 70. | 3-cyanophenyl | tert-butyl |
| 71. | 2-cyano-4,5-dimethoxyphenyl | tert-butyl |
| 72. | 4-cyanophenyl | tert-butyl |
| 73. | 4-aminocarbonyl-3-methoxyphenyl | tert-butyl |
| 74. | 4-(N-hydroxyethylamino)carbonyl-3-methoxyphenyl | tert-butyl |
| 75. | 3-methoxy-4-pentafluoroethylphenyl | tert-butyl |
| 76. | 2-methoxycarbonyl-4,5-dimethoxyphenyl | tert-butyl |
| 77. | 6-methoxy-8-quinolyl | tert-butyl |
| 78. | 2-(3,4,5-trimethoxyphenyl) | adamantyl |
| 79. | 4-(3-Dimethylamino-propoxy)-phenyl | tert-butyl |
| 80. | 3,5-Dimethoxy-4-[2-(4-methyl-piperazin-1-yl)ethoxy]phenyl | phenyl |
| 81. | 3,5-Dimethoxy-4-[3-(4-methyl-piperazin-1-yl)propoxy]phenyl | cyclohexyl |
| 82. | 3-Methoxy-4-[3-(4-methyl-piperazin-1-yl)-propoxy]phenyl | tert-butyl |
| 83. | 3-Methoxy-4-[2-(4-methyl-piperazin-1-yl)-ethoxy]phenyl | adamantyl |
| 84. | 2-Methyl-4-(4-methyl-piperazin-1-yl)-phenyl | tert-butyl |
| 85. | 4-(4-Isopropyl-piperazin-1-yl)-phenyl | cyclohexyl |
| 86. | 3-Fluoro-4-(4-methyl-piperazin-1-yl)-phenyl | phenyl |
| 87. | 3-Fluoro-4-(3-piperidin-1-yl-propoxy)-phenyl | adamantyl |
| 88. | 3,4-Dimethoxy-5-[3-(4-methyl-piperazin-1-yl)-propoxy]-phenyl | cyclohexyl |
| 89. | 3-Methoxy-4-(1-methyl-piperidin-4-ylmethoxy)-phenyl | tert-butyl |
| 90. | 3-Methoxy-4-[2-(1-methyl-piperidin-4-yl)-ethoxy]-phenyl | phenyl |
| 91. | 4-(1-tert-butoxycarbonyl-piperazin-4-yl)phenyl | adamantyl |
| 92. | 4-(4-piperazinyl)phenyl | cyclohexyl |
| 93. | 4-(1-tert-butoxycarbonyl-piperazin-4-yl)-3-difluoromethoxy-phenyl | tert-butyl |
| 94. | 3-Fluoro-4-(2-piperidin-1-yl-ethoxy)-phenyl | phenyl |
| 95. | 3-Fluoro-4-[2-(4-methyl-piperazin-1-yl)-ethoxy]-phenyl | adamantyl |
| 96. | 3-Fluoro-4-[3-(4-methyl-piperazin-1-yl)-propoxy]-phenyl | cyclohexyl |
| 97. | 4-[2-(4-Methyl-piperazin-1-yl)-ethoxy]-phenyl | tert-butyl |
| 98. | 3,5-Dimethoxy-4-(2-morpholin-4-yl-ethoxy)-phenyl | phenyl |
| 99. | 3,5-Dimethoxy-4-(2-piperidin-1-yl-ethoxy)-phenyl | adamantyl |
| 100. | 2-Methyl-4-(3-piperidin-1-yl-propoxy)-phenyl | cyclohexyl |

TABLE 2-continued

Structure: R²-NH-[pyrimidine]-NH-[isoxazole]-R³

| # | R² | R³ |
|---|---|---|
| 101. | 2-Methyl-4-[3-(4-methyl-piperazin-1-yl)-propoxy]-phenyl | tert-butyl |
| 102. | 2-Fluoro-4,5-dimethoxy-phenyl | phenyl |
| 103. | 2-anthracenyl | tert-butyl |
| 104. | 2-benzimidazolyl | phenyl |
| 105. | Phenanthren-3-yl | cyclohexyl |
| 106. | 7-HOSO₂-naphth-2-yl | adamantyl |
| 107. | 3-carbazolyl | tert-butyl |
| 108. | 2-phenanthrenyl | phenyl |
| 109. | 5-HOSO₂-2-naphthyl | cyclohexyl |
| 110. | 8-HOSO₂-2-naphthyl | adamantyl |
| 111. | 2-HOSO₂-6-Naphthyl | tert-butyl |
| 112. | 6-(4-Chlorophenoxy)Pyridin-3-yl | phenyl |
| 113. | 6-(3-Pyridyloxy)Pyridin-3-yl | adamantyl |
| 114. | 6-(4-Chloro-2-Cyclohexylphenoxy)Pyridin-3-yl | cyclohexyl |
| 115. | 2-(2-Pyridyl)Benzimidazol-5-yl | tert-butyl |
| 116. | 2-dibenzofuryl | adamantyl |
| 117. | 2-Phenylbenzoxazol-6-yl | phenyl |
| 118. | 2,3-bis(4-methoxyphenyl)quinoxalin-6-yl | cyclohexyl |
| 119. | 2-dibenzofuryl | tert-butyl |
| 120. | 1,1-dioxobenzo[b]thiophen-6-yl | cyclohexyl |
| 121. | 1-[(4-Methylphenyl)sulfonyl]-1H-indol-5-yl | phenyl |

TABLE 3

Structure: R²-NH-[pyrimidine]-NH-[isoxazole]-R³

| # | R² | R³ |
|---|---|---|
| 122. | 3-quinolyl | tert-butyl |
| 123. | 6-quinolyl | tert-butyl |
| 124. | 2,5-dimethoxyphenyl | tert-butyl |
| 125. | 2-chloro-5-methoxyphenyl | tert-butyl |
| 126. | 4-methoxy-2-methylphenyl | phenyl |
| 127. | 5-methoxy-2-methylphenyl | cyclohexyl |
| 128. | 3-trifluoromethoxyphenyl | adamantyl |
| 129. | 3-(1,1,2,2-tetrafluoroethoxy)phenyl | tert-butyl |
| 130. | 4-trifluoromethoxyphenyl | phenyl |
| 131. | 6-indazolyl | cyclohexyl |
| 132. | 5-benzimidazolyl | tert-butyl |
| 133. | 1-methyl-5-indazolyl | isopropyl |
| 134. | 2-methyl-2H-indazol-5-yl | phenyl |
| 135. | 3-isopropylphenyl | cyclohexyl |
| 136. | 3,5-dimethoxyphenyl | adamantyl |
| 137. | 3,4-dimethoxyphenyl | tert-butyl |
| 138. | 1-methoxy-3-naphthyl | phenyl |
| 139. | 1-(4-Methylpiperazino)isoquinolin-3-yl | cyclohexyl |
| 140. | 2-Phenyl-6-quinoxalinyl | adamantyl |
| 141. | 2-(4-Dimethylamino-phenyl)-benzooxazol-5-yl | tert-butyl |
| 142. | 2-Phenyl-3H-benzoimidazol-5-yl | phenyl |
| 143. | 1-(2-Hydroxyethyl)-2-methyl-1H-benzoimidazol-5-yl | cyclohexyl |
| 144. | [4,5-dihydro-4-carboxy-thiazol-2-yl]-benzothiazol-6-yl | adamantyl |
| 145. | 3-(Aminocarbonyl)-1H-indol-5-yl | tert-butyl |

Although the pharmacological properties of the compounds of Formulas I–IV vary with structural change, in general, activity possessed by compounds of Formulas I–IV may be demonstrated in vivo. The pharmacological properties of the compounds of this invention may be confirmed by a number of pharmacological in vitro assays. The exemplified pharmacological assays which follow have been carried out with the compounds according to the invention and their derivatives.

Biological Evaluation

Kinase Inhibition

The compounds described herein are screened in the following manner. Kinases suitable for use in the following protocol to determine kinase activity of the compounds described herein include, but are not limited to: Lck, Lyn, Src, Fyn, Syk, Zap-70, Itk, Tec, Btk, EGFR, ErbB2, Kdr, Flt-1, Flt-3, Tek, c-Met, InsR, and AKT.

Kinases are expressed as either kinase domains or full length constructs fused to glutathione S-transferase (GST) or polyHistidine tagged fusion proteins in either *E. coli* or Baculovirus-High Five expression systems. They are purified to near homogeneity by affinity chromatography essentially as previously described (Lehr et al., 1996; Gish et al., 1995). In some instances, kinases are co-expressed or mixed with purified or partially purified regulatory polypeptides prior to measurement of activity.

Kinase activity and inhibition are measured essentially by established protocols (Braunwalder et al., 1996). Briefly, the transfer of $^{33}PO_4$ from ATP to the synthetic substrates poly(Glu, Tyr) 4:1 or poly(Arg, Ser) 3:1 attached to the bioactive surface of microtiter plates serves as the basis to evaluate enzyme activity. After an incubation period, the amount of phosphate transferred is measured by first washing the plate with 0.5% phosphoric acid, adding liquid scintillant, and then counting in a liquid scintillation detector. The $IC_{50}$ is determined by the concentration of compound that causes a 50% reduction in the amount of $^{33}P$ incorporated onto the substrate bound to the plate.

Other similar methods whereby phosphate is transferred to peptide or polypeptide substrate containing tyrosine, serine, threonine, or histidine, either alone, in combination, or in combination with other amino acids, in solution or immobilized (i.e., solid phase) are also useful. For example, transfer of phosphate to a peptide or polypeptide can also be detected using scintillation proximity (Wu et al., 2000), ELISA (Cleaveland et al., 1990), Fluorescence Polarization (Seethala and Menzel, 1998), and homogeneous time-resolved fluorescence (HTRF, Kolb et al., 1998). Alternatively, kinase activity can be measured using antibody-based methods whereby an antibody or polypeptide is used as a reagent to detect phosphorylated target polypeptide. Compounds of the present invention showed inhibition of IGF-1R kinase at doses less than 50 μM.

The compounds of examples 1–3, and 14–18 inhibited IGF-1R kinase at a level below 100 nM ($IC_{50}$).

References

Braunwalder et al. (1996). *Anal. Biochem.* 234(1):23–26.
Cleaveland et al. (1990). *Anal Biochem.* 190(2):249–53.
Gish et al. (1995). *Protein Eng.* 8(6):609–614.
Kolb et al. (1998). *Drug Discov. Today.* 3:333–342.
Lehr et al. (1996). *Gene* 169(2):27527–9.
Seethala et al. (1998). *Anal Biochem.* 255(2):257–62.
Wu et al. (2000). *Comb Chem High Throughput Screen.* 3(1):27–36.

IGF-1R Assay Summary Protocols

IGF-1-Induced DNA Synthesis

Human tumor cell lines or a rat fibroblast cell line are plated out in flat-well plates in complete medium and allowed to adhere overnight. The cells are then starved in medium containing 0.1% bovine serum albumin (BSA) overnight, pre-incubated for 1 h with or without dilutions of compound, then activated overnight with 50 ng/mL insulin-like growth factor (IGF-1). Proliferation is determined by the level of $^3$H-thymidine incorporation into DNA. $IC_{50}$'s are determined by comparing the level of thymidine incorporation found in the presence of compound compared to controls.

Examples 14–15 and 17–18 inhibited 3T3 proliferation at a level below 150 nM.

IGF-1R Auto-phosphorylation

Murine fibroblast cells stably transfected with the human IGF-1R are plated out in flat-well plates in complete media and allowed to adhere overnight. The cells are then starved in medium containing 0.1% bovine serum albumin, pre-incubated with or without dilutions of compound, then activated for 5 min with 100 ng/mL IGF-1. The cells are lysed and proteins are separated by SDS-PAGE. The level of phosphotyrosine on IGF-1R β-chain is determined by western blotting with an anti-phospho-IGF-1R β-specific antibody. $IC_{50}$'s are determined by comparing the level of phosphotyrosine found in the presence of compound compared to controls.

Representative compounds tested under the following example protocols exhibit cellular activities consistent with their observed enzyme inhibition activities.

Formulations

Also embraced within this invention is a class of pharmaceutical compositions comprising the active compounds of Formula I in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units were tablets or capsules. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The amount of compounds which were administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg body weight, preferably between about 0.5 and about 50 mg/kg body weight and most preferably between about 0.1 to 20 mg/kg body weight, may be appropriate may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at Least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients were dissolved or suspended in suitable carrier, especially an aqueous solvent for the active ingredients. The active ingredients were preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Pharmaceutical compositions of this invention comprise a compound of the formulas described herein or a pharmaceutically acceptable salt thereof; an additional agent selected from a kinase inhibitory agent (small molecule, polypeptide, antibody, etc.), an immunosuppressant, an anti-cancer agent, an anti-viral agent, antiinflammatory agent, antifungal agent, antibiotic, or an anti-vascular hyperproliferation compound; and any pharmaceutically acceptable carrier, adjuvant or vehicle. Alternate compositions of this invention comprise a compound of the formulae described herein or a pharmaceutically acceptable salt thereof; and a pharmaceutically acceptable carrier, adjuvant or vehicle. Such compositions may optionally comprise one or more additional therapeutic agents, including, for example, kinase inhibitory agents (small molecule, polypeptide, antibody, etc.), immunosuppressants, anti-cancer agents, anti-viral agents, antiinflammatory agents, antifungal agents, antibiotics, or anti-vascular hyperproliferation compounds.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but were not limited to, ion exchangers, alumina, aluminum stearate, lecithin, self-emulsifying drug delivery systems (SEDDS) such as d-a-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which were commonly used include lactose and corn starch. Lubricating agents, such as magnesium stearate, were also typically added. For oral administration in a capsule form, useful diluents include lactose and dried corn starch. When aqueous suspensions and/or emulsions were administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may comprise formulations utilizing liposome or microencapsulation techniques. Such techniques were known in the art.

The pharmaceutical compositions of this invention may be administered by nasal aerosol or inhalation. Such compositions were prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

All mentioned references, patents, applications and publications, are hereby incorporated by reference in their entirety, as if here written.

What is claimed is:

1. A compound of Formula I

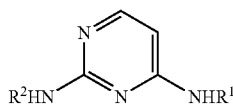

I wherein $R^1$ is isoxazolyl, wherein $R^1$ is optionally substituted with 1–2 substituents independently selected from $R^3$;

wherein $R^2$ is selected from $R^4$ and phenyl optionally substituted with 1–4 substituents independently selected from $R^3$;

wherein $R^3$ is independently selected from $C_{1-4}$-alkyl, $C_{2-4}$-alkenyl, $C_{2-4}$-alkynyl, phenyl, $R^4$, chloro, fluoro, bromo, trifluoromethyl, $C_{1-4}$-alkoxy, phenoxy, heterocyclyloxy, benzyloxy, $C_{1-4}$-alkylcarbonyloxy, amino, alkylamino, phenylamino, carboxy, $C_{1-4}$-alkoxycarbonyl, nitro, cyano, $C_{1-4}$-alkylcarbonyl, aminocarbonyl, $C_{1-4}$-alkylaminocarbonyl, $C_{1-4}$-alkylsulfonyl, $C_{1-4}$-alkylaminosulfonyl, benzyl, $C_{1-4}$-alkoxyalkyl, $C_{1-4}$-aminoalkyl, $C_{1-4}$-alkylaminoalkyl, and 5–6-membered heterocyclyl-$C_{1-4}$-alkyl;

wherein $R^4$ is independently a 6 membered monocyclic, or 8–10 membered bicyclic saturated, partially saturated or unsaturated ring system comprising 1–3 heteroatoms if monocyclic, 1–6 heteroatoms if bicyclic, said heteroatoms independently selected from O, N, or S, which may be saturated or unsaturated, and wherein 0, 1, 2 or 3 atoms of each ring may be substituted by a substituent independently selected from $C_{1-4}$-alkyl, halo, $C_{1-6}$-haloalkyl, oxo, $OR^5$, $NR^5R^5$, $COOR^5$, nitro, cyano, $S(O)_nR^5$, $S(O)_nNR^5R^5$, $C(O)R^5$ and $C(O)NR^5R^5$; and wherein $R^5$ is selected from H, $C_{1-6}$-alkyl, and phenyl optionally substituted with 1–3 substituents independently selected from $C_{1-4}$-alkyl, chloro, fluoro, —$CF_3$, hydroxy, $C_{1-4}$-alkoxy, amino, $C_{1-4}$-alkylamino, carboxy, $C_{1-4}$-alkoxycarbonyl, nitro, cyano, $C_{1-4}$-alkylcarbonyl, $C_{1-4}$-alkylamnocarbonyl, aminocarbonyl, aminosulfonyl and acetyl; or a pharmaceutically acceptable salt thereof.

2. The compound of claim 1 wherein $R^1$ is isoxazolyl, wherein $R^1$ is optionally substituted with 1–2 substituents independently selected from $R^3$;

wherein $R^2$ is selected from $R^4$ and phenyl optionally substituted with 1–4 substituents independently selected from $R^3$;

wherein $R^3$ is independently selected from methyl, ethyl, propyl, tert-butyl, isopropyl, phenyl, chloro, fluoro, bromo, —$CF_3$, methoxy, phenoxy, benzyloxy, acetyl, amino, methylamino, phenylamino, carboxy, cyclohexyl, ethoxycarbonyl, nitro, cyano, methylcarbonyl, aminocarbonyl, methylaminocarbonyl, methylsulfonyl, methylaminosulfonyl, benzyl, methoxymethyl, aminomethyl, N,N-dimethylaminoethyl and furylmethyl; and wherein $R^4$ is independently selected from quinolyl, isoquinolyl, indazolyl, benzimidazolyl, indolyl, isoindolyl, purinyl, and naphthyridinyl, wherein $R^4$ is optionally substituted by a substituent independently selected from methyl, isopropyl, tert-butyl, fluoro, chloro, —$CF_3$, oxo, methoxy, phenoxy, benzyloxy, amino, methylamino, phenylamino, carboxy, ethoxycarbonyl, nitro, cyano, methylcarbonyl, aminocarbonyl, methylaminocarbonyl, methylsulfonyl and methylaminosulfonyl; or a pharmaceutically acceptable salt thereof.

3. Compound of claim 2 wherein $R^2$ is selected from 3,4,5-trimethoxyphenyl, 3,4-dimethoxyphenyl, 2,5-dimethoxyphenyl, 3,4-dimethoxy-6-methylphenyl, quinolinyl, benzimidazolyl, indazolyl, 3-aminosulfonylphenyl and 4-aminosulfonylphenyl; or a pharmaceutically acceptable salt thereof.

4. A compound of Formula II

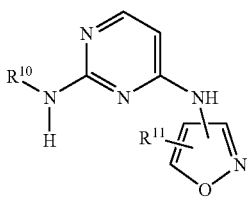

wherein $R^{10}$ is selected from phenyl, and 6–10 membered heterocyclyl; wherein $R^{10}$ is optionally substituted with 1–2 substituents selected from $R^{11}$;

wherein $R^{11}$ is selected from $C_1$–$C_4$ alkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, $CF_3$, —$OR^{12}$, —$OC(O)R^{12}$, —$NR^{12}R^{12}$, —$COOR^{12}$, —$C(O)R^{12}$, —$C(O)NR^{12}R^{12}$, —$SO_2R^{12}$, —$SO_2NR^{12}R^{12}$, —$NR^{12}C(O)NR^{12}R^{12}$, —$NR^{12}C(O)R^{12}$, —$NR^{12}(COOR^{12})$, —$NR^{12}SO_2NR^{12}R^{12}$, —$NR^{12}SO_2R^{12}$, —$OC(O)NR^{12}R^{12}$, $C_1$–$C_3$ alkyl substituted with 1–3 substituents independently selected from optionally substituted phenyl and optionally substituted 5–6 membered heterocyclyl; and $C_2$–$C_3$ alkenyl substituted with 1–3 substituents independently selected from optionally substituted phenyl and optionally substituted 5–6 membered heterocyclyl;

wherein $R^{12}$ is selected from H, $C_{1-6}$-alkyl, and phenyl optionally substituted with 1–3 substituents independently selected from $C_{1-4}$-alkyl, chloro, fluoro, —$CF_3$, hydroxy, $C_{1-4}$-alkoxy, amino, $C_{1-4}$-alkylamino, carboxy, $C_{1-4}$-alkoxycarbonyl, nitro, cyano, $C_{1-4}$-alkylcarbonyl, $C_{1-4}$-alkylaminocarbonyl, aminocarbonyl, aminosulfonyl and acetyl; or a pharmaceutically acceptable salt thereof.

5. A compound of Formula III

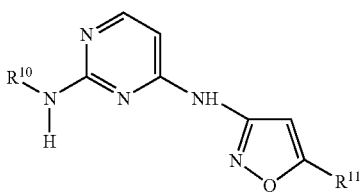

wherein $R^{10}$ is selected from phenyl, and 5–10 membered heterocyclyl; wherein $R^{10}$ is optionally substituted with 1–2 substituents selected from $R^{11}$;

wherein $R^{11}$ is selected from $C_1$–$C_4$ alkyl, $C_2$–$C_3$ alkenyl, $C_2$–$C_3$ alkynyl, $C_3$–$C_6$ cycloalkyl, $C_4$–$C_6$ cycloalkenyl, phenyl, 5–6 membered heterocyclyl, fluoro, chloro, $CF_3$, —$OR^{12}$, —$OC(O)R^{12}$, —$NR^{12}R^{12}$, —$COOR^{12}$, —$C(O)R^{12}$, —$C(O)NR^{12}R^{12}$, —$SO_2R^{12}$, —$SO_2NR^{12}R^{12}$, —$NR^{12}C(O)NR^{12}R^{12}$, —$NR^{12}C(O)R^{12}$, —$NR^{12}(COOR^{12})$, —$NR^{12}SO_2NR^{12}R^{12}$, —$NR^{12}SO_2R^{12}$, —$OC(O)NR^{12}R^{12}$, $C_1$–$C_3$ alkyl substituted with 1–3 substituents independently selected from optionally substituted phenyl and optionally substituted 5–6 membered heterocyclyl; and $C_2$–$C_3$ alkenyl substituted with 1–3 substituents independently selected from optionally substituted phenyl and optionally substituted 5–6 membered heterocyclyl;

wherein $R^{12}$ is selected from H, $C_{1-6}$-alkyl, and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, nitro, cyano, $C_{1-4}$-alkylcarbonyl, $C_{1-4}$-alkylaminocarbonyl, aminocarbonyl, aminosulfonyl and acetyl;

or a pharmaceutically acceptable salt thereof.

6. A compound of Formula I'

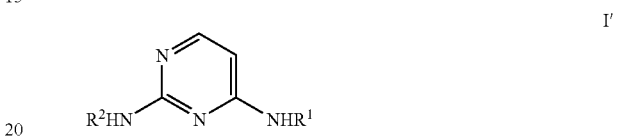

wherein $R^1$ is isoxazolyl, where $R^1$ is optionally substituted with 1–3 substituents independently selected from $R^3$;

wherein $R^2$ is selected from $R^4$ and aryl optionally substituted with 1–3 substituents independently selected from $R^3$;

wherein $R^3$ is independently selected from $C_{1-4}$-alkyl, $C_{2-4}$-alkenyl, $C_{2-4}$-alkynyl, phenyl, $C_{6-10}$-cycloalkyl, $R^4$, chloro, fluoro, bromo, trifluoromethyl, $C_{1-4}$-alkoxy, phenoxy, heterocyclyloxy, benzyloxy, $C_{1-4}$-alkylcarbonyloxy, amino, alkylamino, phenylamino, carboxy, $C_{1-4}$-alkoxycarbonyl, nitro, cyano, $C_{1-4}$-alkylcarbonyl, aminocarbonyl, $C_{1-4}$-alkylaminocarbonyl, $C_{1-4}$-alkylsulfonyl, $C_{1-4}$-alkylaminosulfonyl, benzyl, $C_{1-4}$-alkoxyalkyl, $C_{1-4}$-aminoalkyl, $C_{1-4}$-alkylaminoalkyl, and 5–6-membered heterocyclyl-$C_{1-4}$-alkyl;

wherein $R^4$ is independently 2,3-dihydro-indolyl, 1,3-benzodioxolyl, indolyl, 1,3-dioxo-isoindolyl, indazolyl, quinolyl, isoquinolyl, benzothiazolyl, 1,2,3-benzotriazolyl, benzimidazolyl, and pyridyl; wherein $R^4$ is optionally substituted with hydroxy, $C_{1-3}$-alkoxy, cyano, nitro, halo, $C_{1-3}$-alkyl, di-$C_{1-3}$-alkylamino, di-$C_{1-3}$-alkylamino-$C_{1-3}$-alkyl, di-$C_{1-3}$-alkylamino-$C_{1-3}$-alkoxy, $C_{1-3}$-alkylcarbonyl, $C_{1-3}$-alkoxycarbonyl, $C_{1-3}$-alkylcarbonylamino, pyrrolidinylcarbonyl-$C_{2-3}$-alkenyl, pyrrolidinylcarbonyl-$C_{1-3}$-alkyl, pyrrolidinyl-$C_{1-3}$-alkyl, $C_{2-3}$-alkynyl, acetyl, $C_{1-3}$-alkylcarbonyl-$C_{1-3}$-alkyl, carboxy-$C_{1-3}$-alkyl, (piperidinyl)-$C_{1-3}$-alkoxy, (piperazinyl)-$C_{1-3}$-alkoxy, 2-morpholinyl-$C_{1-3}$-alkoxy, $C_{1-3}$-haloalkyl, $C_{1-3}$-haloalkoxy, aminocarbonyl, aminosulfonyl, $C_{1-3}$-alkylaminosulfonyl, hydroxy-$C_{1-3}$-alkylaminosulfonyl, (thiazolyl)aminosulfonyl, $C_{1-4}$-alkylaminosulfonyl, $C_{1-3}$-alkylcarbonylaminosulfonyl, $C_{1-3}$-alkylsulfonyl, $C_{1-3}$-alkoxycarbonyl-piperazinyl, morpholinyl, $C_{1-3}$-alkylpiperzinyl, piperazinyl, $C_{1-3}$-alkyl-piperazinyl, and oxazolyl; or a pharmaceutically acceptable salt thereof.

7. The compound of claim 6 wherein $R^1$ is isoxazolyl, wherein $R^1$ is optionally substituted with 1–2 substituents independently selected from $R^3$;

wherein $R^2$ is selected from naphthyl, 2,3-dihydro-indolyl, 1,3-benzodioxolyl, indolyl, 1,3-dioxo-isoindolyl, indazolyl, pyridyl, quinolyl, isoquinolyl, benzothiazolyl, 1,2,3-benzotriazolyl, benzimidazolyl, and phenyl; wherein $R^2$ is optionally substituted with 1–3 substituents independently selected from $R^3$;

wherein R³ is independently selected from H, halo, C₁₋₃-alkyl, C₂₋₃-alkenyl, C₂₋₃-alkynyl, phenyl, C₆₋₁₀-cycloalkyl, hydroxy, C₁₋₃-haloalkoxy, C₁₋₃-alkoxy, —C(O)—C₁₋₃-alkyl, and C₁₋₃-haloalkyl; or a pharmaceutically acceptable salt thereof.

8. The compound of claim 7 wherein R¹ is isoxazolyl, wherein R¹ is optionally substituted with 1–2 substituents independently selected from R³;
  wherein R² is selected from 2-naphthyl, 2,3-dihydroindol-6-yl, 1,3-benzodioxol-5-yl, 5-indolyl, 4-indolyl, 1,3-dioxo-isoindol-5-yl, 5-indazolyl, 6-indazolyl, 3-pyridyl, 3-quinolyl, 6-quinolyl, isoquinolyl, benzothiazol-6-yl, benzothiazol-5-yl, 1,2,3-benzotriazol-5-yl, 6-benzimidazolyl, 5-pyridyl, and phenyl;
  wherein R² is optionally substituted with 1–3 substituents independently selected from hydroxy, methoxy, ethoxy, cyano, nitro, chloro, fluoro, bromo, dimethylamino, dimethylaminoethyl, 3-dimethylamino-propoxy, methoxycarbonyl, methylcarbonyl, methylcarbonylamino, CH₃C(O)N(CH₃), methyl, ethyl, isopropyl, pyrrolidin-1-ylcarbonylethenyl, pyrrolidin-1-ylcarbonylethyl, pyrrolidin-1-ylpropyl, ethynyl, acetyl, ethoxycarbonylbutyl, carboxybutyl, 2-(1-methyl-piperidin-4-yl)-ethoxy, 2-(4-methyl-piperazin-1-yl)ethoxy, 3-(4-methyl-piperazin-1-yl)-propoxy, 3-(piperidin-1-yl) propoxy, 2-piperidin-1-yl-ethoxy, 2-morpholin-4-yl-ethoxy, pentafluoroethyl, trifluoromethyl, trifluoromethoxy, difluoromethoxy, aminocarbonyl, aminosulfonyl, N,N'-di-propylaminosulfonyl, hydroxypropylaminosulfonyl, (2-thiazolyl)aminosulfonyl, butylaminosulfonyl, methylcarbonylaminosulfonyl, methylsulfonyl, 1-methyl-piperidin-4-ylmethoxy, 1-tert-butoxycarbonyl-piperazin-4-yl, 4-morpholinyl, 4-methylpiperzin-1-yl, 4-piperazinyl, 4-isopropyl-piperazin-1-yl, and oxazol-5-yl; and
  wherein R³ is independently selected from H, hydroxy, iodo, methyl, acetyl, trifluoromethyl, methoxy, cyclohexyl, adamantyl, phenyl and trifluoromethoxy; or a pharmaceutically acceptable salt thereof.

9. Compound of claim 6 wherein R² is selected from 3,4,5-trimethoxyphenyl, 3,4-dimethoxyphenyl, 2,5-dimethoxyphenyl, 3,4-dimethoxy-6-methylphenyl, 3-methylcarbonylaminophenyl, 4-[CH₃C(O)NH—SO₂]-phenyl, 3-isopropylphenyl, 4-[CH₃C(O)N(CH₃)]phenyl, 3-methoxy-4-morpholinylphenyl, 3-quinolinyl, 6-quinolinyl, benzimidazolyl, 5-indazolyl, 6-indazolyl, 3-chlorophenyl, 3-aminosulfonylphenyl and 4-aminosulfonylphenyl; or a pharmaceutically acceptable salt thereof.

10. Compound of claim 6 wherein R¹ is substituted isoxazolyl; or a pharmaceutically acceptable salt thereof.

11. Compound of claim 6 wherein R¹ is 3-isoxazolyl substituted with a substituent selected from cyclohexyl, adamantyl, phenyl and tert-butyl; or a pharmaceutically acceptable salt thereof.

12. Compound of claim 6 wherein R¹ is 5-isoxazolyl substituted with a substituent selected from cyclohexyl, adamantyl, phenyl and tert-butyl; or a pharmaceutically acceptable salt thereof.

13. Compound of claim 6 and pharmaceutically acceptable salts thereof selected from
  N⁴-(5-tert-butylisoxazol-3-yl)-N²-(3,4,5-trimethoxy-phenyl)-pyrimidine-2,4-diamine;
  N⁴-(5-t-butyl-isoxazol-3-yl)-N²-(4,5-dimethoxy-2-methyl-phenyl)-pyrimidine-2,4-diamine;
  N⁴-(5-t-butyl-isoxazol-3-yl)-N²-(1H-indazol-5-yl)-pyrimidine-2,4-diamine;
  N²-(3-methoxy-4-morpholin-4-yl-phenyl)-N⁴-(5-phenyl-isoxazol-3-yl)-pyrimidine-2,4-diamine;
  N²-(3,4,5-trimethoxyphenyl)-N⁴-(5-phenylisoxazol-3-yl)-2,4-pyrimidinediamine;
  N²-(2-methyl-4,5-dimethoxyphenyl)-N⁴-(5-phenylisoxazol-3-yl)-2,4-pyrimidinediamine;
  N²-(4,5-dimethoxy-2-methylphenyl)-N⁴-(5-adamantyl-isoxazol-3-yl)-2,4-pyrimidinediamine; and
  N²-(3,4,5-trimethoxyphenyl)-N⁴-(3-cyclohexylisoxazol-5-yl)-2,4-pyrimidinediamine.

14. A compound of Formula II'

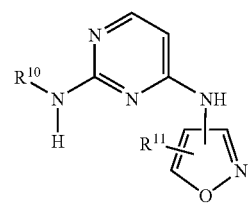

II' wherein R¹⁰ is selected from 3,4,5-trimethoxyphenyl, 3,4-dimethoxy-6-methylphenyl, 3-methoxy-4-morpholinylphenyl and 5-indazolyl;
wherein R¹¹ is selected from C₁–C₄ alkyl, C₂–C₃ alkenyl, C₂–C₃ alkynyl, C₃–C₁₀ cycloalkyl, C₄–C₆ cycloalkenyl, phenyl, 5–6 membered heterocyclyl, fluoro, chloro, CF₃, —OC(O)R¹², —NR¹²R¹², —COOR¹², —C(O)R¹², —C(O)NR¹²R¹², —SO₂R¹², —SO₂NR¹²R¹², —NR¹²C(O)NR¹²R¹², —NR¹²C(O)R¹², —NR¹²(COOR¹²), —NR¹²SO₂NR¹²R¹², —NR¹²SO₂R¹², —OC(O)NR¹²R¹², —OR¹³, C₁–C₃ alkyl substituted with 1–3 substituents independently selected from optionally substituted phenyl and optionally substituted 5–6 membered heterocyclyl; and
  C₂–C₃ alkenyl substituted with 1–3 substituents independently selected from optionally substituted phenyl and optionally substituted 5–6 membered heterocyclyl;
wherein R¹² is selected from H, C₁₋₆-alkyl, and phenyl optionally substituted with 1–3 substituents independently selected from C₁₋₄-alkyl, chloro, fluoro, CF₃, hydroxy, C₁₋₄-alkoxy, amino, C₁₋₄-alkylamino, carboxy, C₁₋₄-alkoxycarbonyl, NO₂, CN, C₁₋₄-alkylcarbonyl, C₁₋₄-alkylaminocarbonyl, aminocarbonyl, aminosulfonyl and acetyl; and
wherein R¹³ is selected from H, C₁₋₆-alkyl, amino-C₁₋₆-alkyl, C₁₋₆-alkylamino-C₁₋₆-alkyl, aminocarbonyl-C₁₋₆-alkyl, C₁₋₆-alkylaminocarbonyl-C₁₋₆-alkyl, and phenyl optionally substituted with 1–3 substituents independently selected from C₁₋₄-alkyl, chloro, fluoro, CF₃, hydroxy, C₁₋₄-alkoxy, amino, C₁₋₄-alkylamino, carboxy, C₁₋₄-alkoxycarbonyl, NO₂, CN, C₁₋₄-alkylcarbonyl, C₁₋₄-alkylaminocarbonyl, aminocarbonyl, aminosulfonyl and acetyl; or a pharmaceutically acceptable salt thereof; provided.

15. A compound of Formula III'

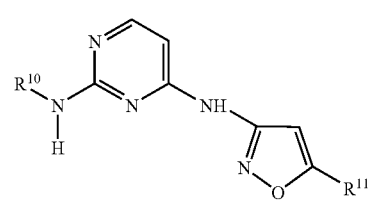

III' wherein $R^{10}$ is selected from phenyl, and 5–10 membered heterocyclyl; wherein $R^{10}$ is optionally substituted with 1–2 substituents selected from $R^{11}$;

wherein $R^{11}$ is selected from $C_1$–$C_4$ alkyl, $C_2$–$C_3$ alkenyl, $C_2$–$C_3$ alkynyl, $C_3$–$C_{10}$ cycloalkyl, $C_4$–$C_6$ cycloalkenyl, phenyl, 5–6 membered heterocyclyl, fluoro, chloro, $CF_3$, —OC(O)$R^{12}$, —N$R^{12}R^{12}$, —COO$R^{12}$, —C(O)$R^{12}$, —C(O)N$R^{12}R^{12}$, —SO$_2R^{12}$, —SO$_2$N$R^{12}R^{12}$, —N$R^{12}$C(O)N$R^{12}R^{12}$, —N$R^{12}$C(O)$R^{12}$, —N$R^{12}$(COO$R^{12}$), —N$R^{12}$SO$_2$N$R^{12}R^{12}$, —N$R^{12}$SO$_2R^{12}$, —OC(O)N$R^{12}R^{12}$, —O$R^{13}$, $C_1$–$C_3$ alkyl substituted with 1–3 substituents independently selected from optionally substituted phenyl and optionally substituted 5–6 membered heterocyclyl; and $C_2$–$C_3$ alkenyl substituted with 1–3 substituents independently selected from optionally substituted phenyl and optionally substituted 5–6 membered heterocyclyl;

wherein $R^{12}$ is selected from H, $C_{1-6}$-alkyl, and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, $NO_2$, CN, $C_{1-4}$-alkylcarbonyl, $C_{1-4}$-alkylaminocarbonyl, aminocarbonyl, aminosulfonyl and acetyl; and wherein $R^{13}$ is selected from H, $C_{1-6}$-alkyl, amino-$C_{1-6}$-alkyl, $C_{1-6}$-alkylamino-$C_{1-6}$-alkyl, aminocarbonyl-$C_{1-6}$-alkyl, $C_{1-6}$-alkylaminocarbonyl-$C_{1-6}$-alkyl, and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, $NO_2$, CN, $C_{1-4}$-alkylcarbonyl, $C_{1-4}$-alkylaminocarbonyl, aminocarbonyl, aminosulfonyl and acetyl; and pharmaceutically acceptable salts thereof; provided $R^{10}$ is not 5-t-butyl-3-isoxazolyl when $R^{11}$ is t-butyl; or a pharmaceutically acceptable salt thereof.

16. Compound of claim 15 wherein $R^{10}$ is selected from 3,4,5-trimethoxyphenyl, 3,4-dimethoxy-6-methylphenyl, 3-methoxy-4-morpholinylphenyl and 5-indazolyl; and wherein $R^{11}$ is selected from cyclohexyl, adamantyl, phenyl and tert-butyl; or a pharmaceutically acceptable salt thereof.

17. A compound of Formula IV

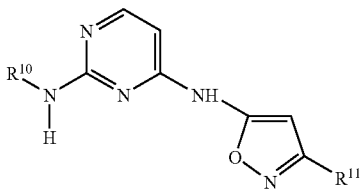

IV wherein $R^{10}$ is selected from phenyl, and 5–10 membered heterocyclyl; wherein $R^{10}$ is optionally substituted with 1–2 substituents selected from $R^{11}$;

wherein $R^{11}$ is selected from $C_1$–$C_4$ alkyl, $C_2$–$C_3$ alkenyl, $C_2$–$C_3$ alkynyl, $C_3$–$C_{10}$ cycloalkyl, $C_4$–$C_6$ cycloalkenyl, phenyl, 5–6 membered heterocyclyl, fluoro, chloro, $CF_3$, —OC(O)$R^{12}$, —N$R^{12}R^{12}$, —COO$R^{12}$, —C(O)$R^{12}$, —C(O)N$R^{12}R^{12}$, —SO$_2R^{12}$, —SO$_2$N$R^{12}R^{12}$, —N$R^{12}$C(O)N$R^{12}R^{12}$, —N$R^{12}$C(O)$R^{12}$, —N$R^{12}$(COO$R^{12}$), —N$R^{12}$SO$_2$N$R^{12}R^{12}$, —N$R^{12}$SO$_2R^{12}$, —OC(O)N$R^{12}R^{12}$, —O$R^{13}$, $C_1$–$C_3$ alkyl substituted with 1–3 substituents independently selected from optionally substituted phenyl and optionally substituted 5–6 membered heterocyclyl; and $C_2$–$C_3$ alkenyl substituted with 1–3 substituents independently selected from optionally substituted phenyl and optionally substituted 5–6 membered heterocyclyl;

wherein $R^{12}$ is selected from H, $C_{1-6}$-alkyl, and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, $NO_2$, CN, $C_{1-4}$-alkylcarbonyl, $C_{1-4}$-alkylaminocarbonyl, aminocarbonyl, aminosulfonyl and acetyl; and wherein $R^{13}$ is selected from H, $C_{1-6}$-alkyl, amino-$C_{1-6}$-alkyl, $C_{1-6}$-alkylamino-$C_{1-6}$-alkyl, aminocarbonyl-$C_{1-6}$-alkyl, $C_{1-6}$-alkylaminocarbonyl-$C_{1-6}$-alkyl, and phenyl optionally substituted with 1–3 substituents independently selected from $C_{1-4}$-alkyl, chloro, fluoro, $CF_3$, hydroxy, $C_{1-4}$-alkoxy, amino, $C_{1-4}$-alkylamino, carboxy, $C_{1-4}$-alkoxycarbonyl, $NO_2$, CN, $C_{1-4}$-alkylcarbonyl, $C_{1-4}$-alkylaminocarbonyl, aminocarbonyl, aminosulfonyl and acetyl; or a pharmaceutically acceptable salts thereof.

18. Compound of claim 17 wherein $R^{10}$ is selected from 3,4,5-trimethoxyphenyl, 3,4-dimethoxy-6-methylphenyl, 3-methoxy-4-morpholinylphenyl and 5-indazolyl; and wherein $R^{11}$ is selected from cyclohexyl, adamantyl, phenyl and tert-butyl; or a pharmaceutically acceptable salt thereof.

19. A pharmaceutical composition comprising a compound according to claim 1 and a pharmaceutically acceptable carrier.

20. A pharmaceutical composition comprising a compound according to claim 2 and a pharmaceutically acceptable carrier.

21. A pharmaceutical composition comprising a compound according to claim 3 and a pharmaceutically acceptable carrier.

22. A pharmaceutical composition comprising a compound according to claim 4 and a pharmaceutically acceptable carrier.

23. A pharmaceutical composition comprising a compound according to claim 5 and a pharmaceutically acceptable carrier.

24. A pharmaceutical composition comprising a compound according to claim 13 and a pharmaceutically acceptable carrier.

25. A pharmaceutical composition comprising a compound according to claim 14 and a pharmaceutically acceptable carrier.

26. A pharmaceutical composition comprising a compound according to claim 15 and a pharmaceutically acceptable carrier.

27. A pharmaceutical composition comprising a compound according to claim 17 and a pharmaceutically acceptable carrier.

28. A method of treating breast cancer in a subject, said method comprising administering an effective amount of a compound of claim 1.

29. A method of treating prostate cancer in a subject, said method comprising administering an effective amount of a compound of claim 1.

* * * * *